US011850535B2

(12) United States Patent
Liu et al.

(10) Patent No.: US 11,850,535 B2
(45) Date of Patent: Dec. 26, 2023

(54) METHODS FOR QUANTITATING INDIVIDUAL ANTIBODIES FROM A MIXTURE

(71) Applicant: Regeneron Pharmaceuticals, Inc., Tarrytown, NY (US)

(72) Inventors: Dingjiang Liu, Pleasantville, NY (US); Lin Luo, Paramus, NJ (US); Long Xu, Shanghai (CN)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/067,803

(22) Filed: Dec. 19, 2022

(65) Prior Publication Data

US 2023/0119592 A1    Apr. 20, 2023

Related U.S. Application Data

(63) Continuation of application No. 17/321,663, filed on May 17, 2021, now Pat. No. 11,571,636, which is a
(Continued)

(51) Int. Cl.
*B01D 15/30* (2006.01)
*G01N 33/68* (2006.01)
(Continued)

(52) U.S. Cl.
CPC ........ *B01D 15/30* (2013.01); *A61K 39/39591* (2013.01); *B01D 15/327* (2013.01);
(Continued)

(58) Field of Classification Search
CPC .................. B01D 15/30; B01D 15/327; A61K 39/39591; C07K 16/00; C07K 16/06;
(Continued)

(56) References Cited

U.S. PATENT DOCUMENTS 4,801,726 A    1/1989 Giese et al.
4,937,188 A    6/1990 Giese et al.
(Continued)

FOREIGN PATENT DOCUMENTS

JP    11-504516    4/1999
JP    2006-523308    10/2006
(Continued)

OTHER PUBLICATIONS

Valliere-Douglass, John F. et al., "Separation of populations of antibody variants by fine tuning of hydrophobic-interaction chromatography operating conditions," J. of Chromatography A, vol. 1214, No. 1-2, 2008, pp. 81-89.
(Continued)

*Primary Examiner* — Jennifer Wecker
*Assistant Examiner* — Michael Paul Shimek
(74) *Attorney, Agent, or Firm* — Bookoff McAndrews, PLLC

(57) ABSTRACT

The present disclosure relates to, inter alia, a method of quantitating an amount of an antibody molecule from a mixture comprising two or more antibody molecules, comprising separating each of the two or more antibody molecules from the mixture by hydrophobic interaction chromatography high performance liquid chromatography (HIC-HPLC) and quantitating an amount of each antibody molecule, wherein the molecular weight of each antibody molecule is within 15 kDa of any other antibody molecule in the mixture and either each antibody molecule is different from another antibody molecule in the mixture by more than about 0.25 unit on the Kyte & Doolittle hydropathy scale or each of the antibody molecules when nm alone on HIC-HPLC elutes at distinct run time with little overlap from the other antibody molecules in the mixture, or both.

20 Claims, 19 Drawing Sheets

Related U.S. Application Data continuation of application No. 16/322,292, filed as application No. PCT/US2017/045855 on Aug. 8, 2017, now Pat. No. 11,020,686.

(60) Provisional application No. 62/375,887, filed on Aug. 16, 2016.

(51) Int. Cl.
  *B01D 15/32* (2006.01)
  *A61K 39/395* (2006.01)
  *C07K 16/00* (2006.01)
  *C07K 16/06* (2006.01)
  *C07K 16/10* (2006.01)
  *G01N 30/02* (2006.01)

(52) U.S. Cl.
  CPC .............. *C07K 16/00* (2013.01); *C07K 16/06* (2013.01); *C07K 16/065* (2013.01); *C07K 16/10* (2013.01); *G01N 30/02* (2013.01); *G01N 33/6854* (2013.01); *G01N 2030/027* (2013.01)

(58) Field of Classification Search
  CPC ...... C07K 16/065; C07K 16/10; G01N 30/02; G01N 33/6854; G01N 2030/027; G01N 30/88; G01N 2030/8831; A61P 11/00; A61P 27/02; A61P 31/12
  See application file for complete search history.

(56) References Cited

U.S. PATENT DOCUMENTS

| | | |
|---|---|---|
| 5,190,864 A | 3/1993 | Giese et al. |
| 5,412,083 A | 5/1995 | Giese et al. |
| 5,641,870 A | 6/1997 | Rinderknecht et al. |
| 6,066,719 A | 5/2000 | Zapata |
| 6,214,984 B1 | 4/2001 | Zapata |
| 6,441,160 B2 | 8/2002 | Kitamura et al. |
| 7,038,017 B2 | 5/2006 | Rinderknecht et al. |
| 7,070,959 B1 | 7/2006 | Papadopoulos et al. |
| 7,101,982 B2 | 9/2006 | Ghose et al. |
| 7,220,356 B2 | 5/2007 | Thommes et al. |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| RE40,070 E | 2/2008 | Shadle et al. |
| 7,374,757 B2 | 5/2008 | Papadopoulos et al. |
| 7,374,758 B2 | 5/2008 | Papadopoulos et al. |
| 7,385,040 B2 | 6/2008 | Johansson et al. |
| 7,393,631 B2 | 7/2008 | Cannon-Carlson et al. |
| 7,427,659 B2 | 9/2008 | Shukla et al. |
| 7,531,173 B2 | 5/2009 | Wiegand et al. |
| 7,608,261 B2 | 10/2009 | Furfine et al. |
| 7,666,413 B2 | 2/2010 | Liu et al. |
| 7,700,097 B2 | 4/2010 | Braslawsky et al. |
| 7,714,112 B2 | 5/2010 | Engstrand et al. |
| 7,750,129 B2 | 7/2010 | Johansson et al. |
| RE41,555 E | 8/2010 | Shadle et al. |
| RE41,595 E | 8/2010 | Shandle et al. |
| 7,795,405 B2 | 9/2010 | DiNovo |
| 7,863,426 B2 | 1/2011 | Wan et al. |
| 7,972,598 B2 | 7/2011 | Daly et al. |
| 8,003,364 B2 | 8/2011 | Post Hansen et al. |
| 8,012,754 B2 | 9/2011 | Rinderknecht et al. |
| 8,029,791 B2 | 10/2011 | Papadopoulos et al. |
| 8,084,032 B2 | 12/2011 | Yumioka et al. |
| 8,092,803 B2 | 1/2012 | Furfine et al. |
| 8,163,531 B2 | 4/2012 | Post Hansen et al. |
| 8,231,876 B2 | 7/2012 | Wan et al. |
| 8,343,349 B2 | 1/2013 | Eriksson et al. |
| 8,343,737 B2 | 1/2013 | Papadopoulos et al. |
| 8,410,928 B2 | 4/2013 | Ganguly et al. |
| 8,435,527 B2 | 5/2013 | Yumioka et al. |
| 8,470,328 B2 | 6/2013 | Yumioka et al. |
| 8,470,578 B2 | 6/2013 | Post Hansen et al. |
| 8,491,904 B2 | 7/2013 | Hickman |
| 8,568,586 B2 | 10/2013 | Cunnien et al. |
| 8,603,473 B2 | 12/2013 | Glaser et al. |
| 8,608,960 B2 | 12/2013 | Thommes et al. |
| 8,647,842 B2 | 2/2014 | Papadopoulos et al. |
| 8,821,865 B2 | 9/2014 | Neu et al. |
| 8,821,879 B2 | 9/2014 | Babuka et al. |
| 8,871,209 B2 | 10/2014 | Stitt |
| 8,895,709 B2 | 11/2014 | Hickman et al. |
| 8,895,710 B2 | 11/2014 | Engstrand et al. |
| 8,946,395 B1 | 2/2015 | Herigstad et al. |
| 8,969,532 B2 | 3/2015 | DeFrees et al. |
| 9,017,687 B1 | 4/2015 | Wang et al. |
| 9,018,361 B2 | 4/2015 | Hickman et al. |
| 9,067,990 B2 | 6/2015 | Wang et al. |
| 9,102,723 B2 | 8/2015 | Wan et al. |
| 9,109,010 B2 | 8/2015 | Hickman et al. |
| 9,109,201 B2 | 8/2015 | Post Hansen et al. |
| 9,150,645 B2 | 10/2015 | Subramanian et al. |
| 9,150,938 B2 | 10/2015 | Oroskar |
| 9,181,572 B2 | 11/2015 | Subramanian et al. |
| 9,193,787 B2 | 11/2015 | Chumsae |
| 9,249,182 B2 | 2/2016 | Herigstad et al. |
| 9,266,950 B2 | 2/2016 | Hickman |
| 9,334,319 B2 | 5/2016 | Ramasubramanyan et al. |
| 9,346,879 B2 | 5/2016 | Ramasubramanyan et al. |
| 9,359,434 B2 | 6/2016 | Subramanian et al. |
| 9,488,625 B2 | 11/2016 | Felgenhauer et al. |
| 9,505,833 B2 | 11/2016 | Chumsae |
| 9,518,082 B2 | 12/2016 | Allison et al. |
| 9,650,411 B2 | 5/2017 | Ishihara |
| 9,650,412 B2 | 5/2017 | Konstantinov et al. |
| 9,650,413 B2 | 5/2017 | Konstantinov et al. |
| 9,657,056 B2 | 5/2017 | Konstantinov et al. |
| 9,683,012 B2 | 6/2017 | Yoon et al. |
| 9,683,033 B2 | 6/2017 | Subramanian et al. |
| 9,688,752 B2 | 6/2017 | Wang et al. |
| 9,708,365 B2 | 7/2017 | Mendiratta et al. |
| 9,708,399 B2 | 7/2017 | Wang et al. |
| 9,708,400 B2 | 7/2017 | Subramanian et al. |
| 9,766,217 B2 | 9/2017 | Kidal et al. |
| 9,878,266 B2 | 1/2018 | Engstrand et al. |
| 9,920,120 B2 | 3/2018 | Yu et al. |
| 9,945,858 B2 | 4/2018 | Gunawan et al. |
| 9,957,318 B2 | 5/2018 | Ramasubramanyan et al. |
| 9,975,948 B2 | 5/2018 | Hickman |
| 9,994,609 B2 | 6/2018 | Ghose et al. |
| 10,017,746 B2 | 7/2018 | Sheldon et al. |
| 10,023,608 B1 | 7/2018 | Ma et al. |
| 10,053,489 B2 | 8/2018 | Kim et al. |
| 10,115,576 B2 | 10/2018 | Geromanos et al. |
| 10,188,732 B2 | 1/2019 | Conley et al. |
| 10,342,876 B2 | 7/2019 | Bak et al. |
| 10,363,496 B2 | 7/2019 | Coutard |
| 10,494,429 B2 | 12/2019 | Yu et al. |
| 10,533,045 B2 | 1/2020 | Allison et al. |
| 10,597,443 B2 | 3/2020 | Schurpf et al. |
| 10,597,446 B2 | 3/2020 | Yu et al. |
| 10,597,447 B2 | 3/2020 | Yu et al. |
| 10,626,376 B2 | 4/2020 | McNally et al. |
| 10,692,709 B2 | 6/2020 | Geromanos et al. |
| 10,696,735 B2 | 6/2020 | Yonan et al. |
| 10,696,952 B2 | 6/2020 | Sheldon et al. |
| 10,702,603 B2 | 7/2020 | Conley et al. |
| 10,788,494 B2 | 9/2020 | Gunawan et al. |
| 10,822,404 B2 | 11/2020 | Yu et al. |
| 10,894,079 B2 | 1/2021 | Mullner et al. |
| 10,940,401 B2 | 3/2021 | Mahajan et al. |
| 10,947,262 B2 | 3/2021 | Gronke et al. |
| 2002/0064860 A1 | 5/2002 | Cannon-Carlson et al. |
| 2004/0106184 A1 | 6/2004 | Senesac |
| 2005/0163782 A1 | 7/2005 | Glaser et al. |
| 2006/0027454 A1 | 2/2006 | DiNovo |
| 2006/0257972 A1 | 11/2006 | Ishihara |
| 2007/0213513 A1 | 9/2007 | Van Alstine et al. |
| 2008/0299545 A1 | 12/2008 | Zhang et al. |
| 2008/0299671 A1 | 12/2008 | Glad et al. |

(56) References Cited

U.S. PATENT DOCUMENTS

| | | |
|---|---|---|
| 2010/0035299 A1 | 2/2010 | DeFrees et al. |
| 2010/0069617 A1 | 3/2010 | Gagnon |
| 2010/0127860 A1 | 5/2010 | Ganguly et al. |
| 2010/0136025 A1 | 6/2010 | Hickman et al. |
| 2010/0278822 A1 | 11/2010 | Fraunhofer et al. |
| 2011/0147312 A1 | 6/2011 | Cunnien et al. |
| 2012/0121581 A1* | 5/2012 | Babuka .................. A61K 47/12 424/133.1 |
| 2013/0131318 A1 | 5/2013 | Kremer et al. |
| 2013/0149310 A1 | 6/2013 | Jasson et al. |
| 2013/0336957 A1 | 12/2013 | Wang et al. |
| 2014/0010820 A1 | 1/2014 | Wang et al. |
| 2014/0045725 A1 | 2/2014 | Muller-Spath et al. |
| 2014/0046038 A1 | 2/2014 | Ishihara |
| 2014/0072585 A1 | 3/2014 | Herigstad et al. |
| 2014/0154270 A1 | 6/2014 | Wang et al. |
| 2014/0302053 A1 | 10/2014 | Huang et al. |
| 2014/0356370 A1 | 12/2014 | Swergold et al. |
| 2014/0356371 A1 | 12/2014 | Swergold et al. |
| 2014/0356372 A1 | 12/2014 | Stahl et al. |
| 2015/0170892 A1 | 6/2015 | Geromanos et al. |
| 2015/0210735 A1 | 7/2015 | Hickman et al. |
| 2015/0299249 A1 | 10/2015 | Herigstad et al. |
| 2015/0337029 A1 | 11/2015 | Kyratsous et al. |
| 2016/0083452 A1 | 3/2016 | Hickman et al. |
| 2016/0101181 A1 | 4/2016 | Bak et al. |
| 2016/0115193 A1 | 4/2016 | Herigstad et al. |
| 2016/0152717 A1 | 6/2016 | Cao et al. |
| 2016/0215040 A1 | 7/2016 | Kyratsous et al. |
| 2016/0251441 A1 | 9/2016 | O'Connor et al. |
| 2016/0320391 A1 | 11/2016 | Gunawan et al. |
| 2017/0101472 A1 | 4/2017 | Ullman et al. |
| 2017/0158760 A1 | 6/2017 | Hickman et al. |
| 2017/0174779 A1 | 6/2017 | Varghese et al. |
| 2017/0174781 A1 | 6/2017 | Brownstein |
| 2017/0342145 A1 | 11/2017 | Wang et al. |
| 2017/0349654 A1 | 12/2017 | Wang et al. |
| 2018/0222938 A1 | 8/2018 | Herigstad et al. |
| 2018/0230210 A1 | 8/2018 | Hickman |
| 2019/0062419 A1 | 2/2019 | Ramasubramanyan et al. |
| 2019/0144495 A1 | 5/2019 | Ghose et al. |
| 2019/0248823 A1 | 8/2019 | Gronke et al. |
| 2019/0298829 A1 | 10/2019 | Wan et al. |
| 2020/0002373 A1 | 1/2020 | Livigini et al. |
| 2020/0223913 A1 | 7/2020 | Allison et al. |
| 2021/0009632 A1 | 1/2021 | Tan et al. |

FOREIGN PATENT DOCUMENTS

| | | |
|---|---|---|
| JP | 2010-515020 | 5/2010 |
| JP | 2013-500483 | 1/2013 |
| JP | 2014-530848 | 11/2014 |
| WO | 96/34015 A1 | 4/1996 |
| WO | WO-9625425 A1 | 8/1996 |
| WO | WO-2007110339 A1 | 10/2007 |
| WO | WO-2009058769 A1 | 5/2009 |
| WO | WO-2010019814 A1 | 2/2010 |
| WO | WO 2011/028961 A2 | 3/2011 |
| WO | WO-2011098526 A1 | 8/2011 |
| WO | WO-2012030512 A1 | 3/2012 |
| WO | WO-2012065072 A2 | 5/2012 |
| WO | WO-2013066707 A1 | 5/2013 |
| WO | WO-2013078170 A1 | 5/2013 |
| WO | 2013/088259 A2 | 6/2013 |
| WO | WO-2013176754 A1 | 11/2013 |
| WO | WO-2013177115 A2 | 11/2013 |
| WO | WO-2013177118 A2 | 11/2013 |
| WO | WO-2014100143 A2 | 6/2014 |
| WO | WO-2014143185 A1 | 9/2014 |
| WO | WO-2014158231 A1 | 10/2014 |
| WO | WO-2015035180 A1 | 3/2015 |
| WO | WO-2015038888 A1 | 3/2015 |
| WO | WO 2015/179535 A1 | 11/2015 |
| WO | WO-2017140881 A1 | 8/2017 |
| WO | WO-2018027195 A1 | 2/2018 |
| WO | WO-2019040671 A1 | 2/2019 |
| WO | WO-2019178495 A1 | 9/2019 |
| WO | WO-2019246153 A1 | 12/2019 |
| WO | WO-2020023566 A1 | 1/2020 |
| WO | WO-2020037016 A1 | 2/2020 |
| WO | WO-2020096958 A1 | 5/2020 |
| WO | WO-2020172658 A1 | 8/2020 |
| WO | WO-2020205469 A1 | 10/2020 |
| WO | WO-2020264411 A1 | 12/2020 |

OTHER PUBLICATIONS

Valliere-Douglass, John F. et al., "Separation and Characterization of an IgG2 Antibody Containing a Cyclic Imide in CDR1 of Light Chain by Hydrophobic Interaction Chromatography and Mass Spectrometry," Anal. Chem. 2008, vol. 80, No. 9, May 1, 2008, pp. 3168-3174.

Boyd, Daniel et al., "HIC resolution of an IgG1 with an oxidized Trp in a complementarity determining region," J. of Chromatography B, vol. 879, Issues 13-14, Apr. 15, 2011, pp. 955-960.

Ouyang J., "Drug-to-Antibody Ratio (DAR) and Drug Load Distribution by Hydrophobic Interaction Chromatography and Reversed Phase High-Performance Liquid Chromatography," Book, Ducry L. (eds) Antibody-Drug Conjugates. Methods in Molecular Biology (Methods and Protocols), vol. 1045, Jan. 1, 2013, Humana Press, Totowa, NJ.

Ouellette, David et al., "Comparison of the in vitro and in vivo stability of a succinimide intermediate observed on a therapeutic IgG1 molecule," MABS, vol. 5, No. 3, May 1, 2013, pp. 432-444.

Haverick, Mark et al., "Separation of mAbs molecular variants by analytical hydrophobic interaction chromatography HPLC: overview and applications," MABS, vol. 6, No. 4, Apr. 1, 2014, pp. 852-858.

International Search Report and Written Opinion, dated Sep. 18, 2017, in international application No. PCT/US2017/045855 (12 pages).

Nadja Alt et al. "Determination of critical quality attributes for monoclonal antibodies using quality by design principles." Biologicals, 44 (2016) 291-305. Available online Jul. 25, 2016 (15 pages).

Yi Du et al. "Chromatographic analysis of the acidic and basic species of recombinant monoclonal antibodies." mAbs 4:5, 578-585. Published online Jul. 23, 2012 (9 pages).

Szabolcs Fekete et al. "Hydrophobic interaction chromatography for the characterization of monoclonal antibodies and related products." Journal of Pharmaceutical and Biomedical Analysis 130 (2016) 3-18. Available online Apr. 4, 2016 (16 pages).

Whitney P. Kirschbrown et al. "Development of a Subcutaneous Fixed-Dose Combination of Pertuzumab and Trastuzumab: Results From the Phase Ib Dose-Finding Study." J. Clinical Pharmacology 2019, 59(5) 702-716 (16 pages).

Sandra Grotefend et al. "Protein quantitation using various modes of high performance liquid chromatography." J. Pharmaceutical and Biomedical Analysis 71 (2012) 127-138. Available online Aug. 29, 2012 (12 pages).

Kohzoh Imai et al. "Comparing antibody and small-molecule therapies for cancer." Nature Reviews, vol. 6, 714-727, Sep. 2006 (14 pages).

Paul J. Carter et al. "Next generation antibody drugs: pursuit of the 'high-hanging fruit'." Nature Reviews: Drug Discovery, vol. 17, 197-223, Mar. 2018 (27 pages).

Claudia Mueller et al. "Challenges for the pharmaceutical technical development of protein coformulations." Journal of Pharmacy and Pharmacology, 70 (2018), pp. 666-674 (9 pages).

Mingyan Cao et al. "Charge variants characterization and release assay development for co-formulated antibodies as a combination therapy." mAbs 2019, vol. 11, No. 3, 489-499 (11 pages).

James E. Noble et al. Methods in Enzymology, vol. 463, pp. 73-95. "Chapter Eight: Quantitation of Protein." 2009, Elsevier Inc., ISSN 0076-6879 (23 pages).

R.E. Mushens et al. "Quantitation of monoclonal antibodies by ELISA: The use of purified mouse IgG and mouse IgM monoclonal antibodies as standards in a quantitative ELISA measuring mono-

(56) References Cited

OTHER PUBLICATIONS clonal antibodies produced by cell culture." Journal of Immunological Methods, vol. 162, Issue 1, Jun. 4, 1993, pp. 77-83, at Abstract (2 pages).

Hongcheng Liu et al. "Quantitation of recombinant monoclonal antibody in monkey serum by liquid chromatography-mass spectrometry." Analytical Biochemistry 414 (2011) 147-153. Available online Mar. 8, 2011 (7 pages).

Alain Beck et al. "Biosimilar, Biobetter, and Next Generation Antibody Characterization by Mass Spectrometry." Analytical Chemistry 2012, 84, 4637-4646 (10 pages).

Paula M. Ladwig et al. "Mass Spectrometry Approaches for Identification and Quantitation of Therapeutic Monoclonal Antibodies in the Clinical Laboratory." Clinical and Vaccine Immunology, vol. 24, Issue 5, May 2017 (17 pages).

Hyunju Lee et al. "Validation of the World Health Organization Enzyme-Linked Immunosorbent Assay for the Quantitation of Immunoglobulin G Serotype-Specific Anti-Pneumococcal Antibodies in Human Serum." J. Korean Med. Sci. 2017, 32: 1581-1587 (7 pages).

Jack Kyte and Russell F. Doolittle, A Simple Method for Displaying the Hydropathic Character of a Protein, J. Mol. Biol. 157, 105-132 (1982) (28 pages).

Ryan M. Krammer, et al. Toward a Molecular Understanding of Protein Solubility: Increased Negative Surface Charge Correlates with Increased Solubility, Biophys. J., vol. 102, 1907-1915 (Apr. 2012) (9 pages).

Stephen M. Berge, "Pharmaceutical Salts," J. Pharm. Sci. vol. 66, No. 1 (Jan. 1977) (19 pages).

Patricia Estep et al., An Alternative Assay to Hydrophobic Interaction Chromatography for High-Throughput Characterization of Monoclonal Antibodies, mAbs, 7:3, 553-561 (May 1, 2015) (10 pages).

Hari, S.B. et al., "Acid-Induced Aggregation of Human Monoclonal IgG1 and IgG2: Molecular Mechanism and the Effect of Solution Composition," Biochemistry, vol. 49, pp. 9328-9338 (2010).

Basics of liquid chromatography, COSMOSIL, Nacalai Tesque, Inc., Apr. 14, 2010. Retrieved from the Internet: <URL: https://web.archive.org/web/20100414123526/https://www.nacalai.co.jp/cosmosil/technical/01.html> (14 pages).

* cited by examiner

METHODS FOR QUANTITATING INDIVIDUAL ANTIBODIES FROM A MIXTURE

CROSS-REFERENCE TO RELATED APPLICATIONS

This application is a continuation of U.S. application Ser. No. 17/321,663, filed on May 17, 2021, which is a continuation of U.S. application Ser. No. 16/322,292, filed on Jan. 31, 2019, which is a U.S. national stage filing under 35 U.S.C. § 371 of International Application No. PCT/US2017/045855, filed on Aug. 8, 2017, which claims the benefit of priority to U.S. Provisional Application No. 62/375,887, filed on Aug. 16, 2016, each of which are incorporated by reference herein in their entireties.

TECHNICAL FIELD

This disclosure relates to the field of assays for co-formulations of therapeutic antibodies.

BACKGROUND

Administration of multiple, rather than single, monoclonal antibodies (mAbs) to a patient may improve their diagnostic or therapeutic indication and efficacy. These mAbs may be co-formulated in a single drug product (DP) and the DP administered to a patient.

A method is required by regulatory agencies to quantitate the individual mAbs in a co-formulated drug substance (cFDS) to be incorporated into a DP, or a DP itself. Developing a method to separate two or more antibody molecules and to measure the concentration of each mAb is challenging, because the antibody molecules may have similar molecular weights, protein structures, and charge properties.

SUMMARY

This disclosure includes a method of quantitating amounts of antibodies from a mixture comprising a plurality of antibodies. In some aspects, the method may include, among other things, separating each of the plurality of antibodies in the mixture using hydrophobic interaction chromatography high performance liquid chromatography (HIC-HPLC), and quantitating an amount of each antibody in the mixture, wherein a molecular weight of each antibody in the mixture is within 15 kDa of a molecular weight of any other antibodies in the mixture, and either a surface hydrophobicity of each antibody in the mixture is different from a surface hydrophobicity of another antibody in the mixture by more than about 0.25 units on the Kyte & Doolittle hydropathy scale, or each antibody in the mixture, when run on HIC-HPLC individually, elutes at a distinct run time from another antibody in the mixture, or both.

In some embodiments, the surface hydrophobicity of each antibody in the mixture is different from the surface hydrophobicity of each other antibody in the mixture by about 0.5 to about 1.0 units on the Kyte & Doolittle hydropathy scale. In further embodiments, the surface hydrophobicity of each antibody in the mixture is determined by calculating surface hydrophobicity based on protein structure or structural model, rapid screening for solubility in ammonium sulfate or PEG8000, or rapid screening for molecule interaction by affinity capture-self-interaction nanoparticle spectroscopy (AC-SINS).

In additional embodiments, a first antibody in the mixture elutes at a first run time during a HIC-HPLC run, a second antibody in the mixture elutes at a second run time during the HIC-HPLC run, and the first and second run times do not overlap. In yet further embodiments, a first antibody in the mixture and a second antibody in the mixture have protein sequences that are at least 90% homologous, the first antibody and the second antibody have protein structures that are at least 90% homologous, as determined by their protein sequences, or the first antibody and the second antibody have isoelectric points (pI) within about 0.6 of one another, as determined by their protein sequences.

In some embodiments, the plurality of antibodies comprises three antibodies. In further embodiments, one or more of the antibodies in the mixture are monoclonal antibodies. In still further embodiments, one or more of the antibodies in the mixture are human monoclonal antibodies. In other embodiments, two or more of the antibodies in the mixture are of the same isotype. In some embodiments, two or more of the antibodies in the mixture are variants of each other. In further embodiments, two or more of the antibodies in the mixture bind to the same antigen.

In some embodiments, the mixture is a co-formulated composition. In additional embodiments, the co-formulated composition is configured to treat MERS in a human patient. In further embodiments, the co-formulated composition is configured to treat Ebola hemorrhagic fever in a human patient. In further embodiments, the co-formulated composition is configured to treat macular degeneration in a human patient. In yet further embodiments, the two or more antibodies in the co-formulated composition are configured to treat an infectious disease in a human patient. In some embodiments, the co-formulated composition is included in a drug product.

In some embodiments, the HIC-HPLC is performed in a buffer at about pH 5.0 to about pH 7.0. In further embodiments, the method further comprises generating a chromatograph from the HIC-HPLC, wherein for elution of each antibody in the mixture, the chromatograph shows a peak that does not overlap with other peaks in the chromatograph.

This disclosure also includes a method of quantitating amounts of antibodies from a mixture comprising a plurality of antibodies, the method comprising: separating each of the plurality of antibodies in the mixture using hydrophobic interaction chromatography high performance liquid chromatography (HIC-HPLC), wherein a molecular weight of each antibody in the mixture is within 15 kDa of a molecular weight of each other antibody in the mixture; quantitating an amount of each antibody in the mixture; and generating a chromatograph from the HIC-HPLC, wherein for elution of each antibody in the mixture, the chromatograph shows a peak that does not overlap with other peaks in the chromatograph. In some embodiments, one or more of the plurality of antibodies are human monoclonal antibodies. In further embodiments, either a surface hydrophobicity of each antibody in the mixture is different from a surface hydrophobicity of another antibody in the mixture by more than about 0.25 units on the Kyte & Doolittle hydropathy scale, or each antibody in the mixture, when run on HIC-HPLC individually, elutes at a distinct run time from another antibody in the mixture, or both.

Numerous other aspects and embodiments are provided in accordance with these and other aspects of the disclosure. Other features and aspects of the present disclosure will become more fully apparent from the following detailed description and the appended claims.

BRIEF DESCRIPTION OF THE DRAWINGS

The accompanying drawings, which are incorporated in and constitute a part of this specification, illustrate various examples and together with the description, serve to explain the principles of the present disclosure. Any features of an embodiment or example described herein (e.g., device, method, etc.) may be combined with any other embodiment or example, and are encompassed by the present disclosure.

DETAILED DESCRIPTION

Figure 1:
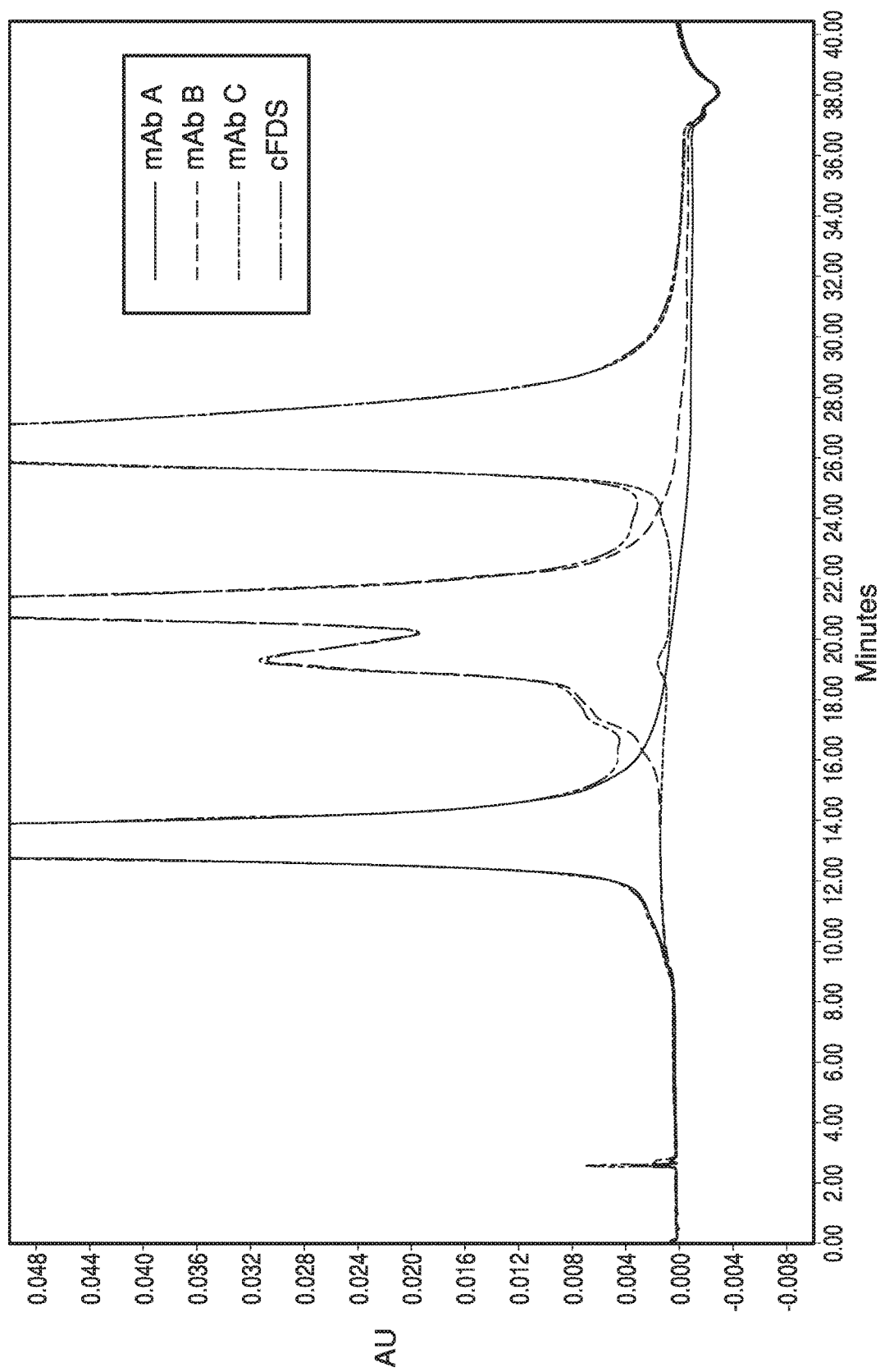
FIG. 1 shows an exemplary chromatograph of a HIC-HPLC run of a co-formulation comprising anti-Ebola mAbs.

The term "antibody" is sometimes used interchangeably with the term "immunoglobulin." Briefly, it may refer to a whole antibody comprising two light chain polypeptides and two heavy chain polypeptides. Whole antibodies include different antibody isotypes including IgM, IgG, IgA, IgD, and IgE antibodies. The term "antibody" may include, for example, a polyclonal antibody, a monoclonal antibody (mAb), a chimerized or chimeric antibody, a humanized antibody, a primatized antibody, a deimmunized antibody, and a fully human antibody. The antibody may be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody may be a purified or a recombinant antibody. The antibody can also be an engineered protein or antibody-like protein containing at least one immunoglobulin domain (e.g., a fusion protein). The engineered protein or antibody-like protein may also be a bi-specific antibody or a tri-specific antibody, or a dimer, trimer, or multimer antibody, or a diabody, a DVD-Ig, a CODV-Ig, an Affibody®, or a Nanobody®.

The terms "variant of an antibody," "antibody variant," and the like, refer to an antibody that varies from another antibody in that the variant antibody is a deletion variant, insertion variant, and/or substitution variant of the other antibody.

The term "human antibody," as used herein, is intended to include antibodies having variable and constant regions derived from human germline immunoglobulin sequences. Human mAbs may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

As used herein, the terms "treat," "treating," or "treatment" refer to the reduction or amelioration of the severity of at least one symptom or indication of a disease or condition due to the administration of a co-formulation of two or more antibodies to a subject in need thereof. The terms include inhibition of progression of disease. The terms also include positive prognosis of disease.

The terms "prevent," "preventing" or "prevention" refer to inhibition of manifestation of a disease or condition any symptoms or indications of that disease or condition upon administration of a co-formulation of two or more antibodies.

For the terms "for example" and "such as," and grammatical equivalences thereof, the phrase "and without limitation" is understood to follow unless explicitly stated otherwise. As used herein, the term "about" and the signifier "—" are meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Antibody molecules, such as monoclonal antibody molecules, may be co-formulated to treat one or more diseases or conditions in a patient (including a human patient). The terms "patient" and "subject" are used interchangeably herein.

A co-formulated drug product (DP) may include a co-formulated drug substance (cFDS) (also referred to herein as a co-formulation) containing two or more (e.g., three) human monoclonal antibody (mAb) molecules. The cFDS is prepared by mixing purified mAbs at a predetermined ratio. A method is required by regulatory agencies to quantitate each of individual mAbs in the cFDS.

The mAb molecules in the co-formulation may be similar to each other: they may be immunoglobulins (such as IgG1) with about the same molecular weight (e.g., ~145 kDa); with similar protein structure and charge properties.

Methods disclosed herein for quantitating similar mAb molecules in a co-formulation are precise, accurate, reproducible, suitable for use in quality control environments, do not use expensive equipment, and do not require cumbersome sample preparation.

Methods

This disclosure provides methods of quantitating an amount of an antibody molecule from a mixture comprising two or more antibody molecules. The method may comprise separating each of the two or more antibody molecules from the mixture by hydrophobic interaction chromatography high performance liquid chromatography (HIC-HPLC) and quantitating an amount of each antibody molecule, wherein the molecular weight of each antibody molecule is within 15 kDa of any other antibody molecule in the mixture and either each antibody molecule is different from another antibody molecule in the mixture by more than about 0.25 units on the Kyte & Doolittle hydropathy scale (see, e.g., Kyte and Doolittle, *J. Mol. Biol.* 157, 105-132 (1982)), or each of the antibody molecules, when run alone on HIC-HPLC, elutes at a distinct run time with little overlap from other antibody molecules in the mixture, or both. In certain embodiments, for example, the relative hydrophobicity of each antibody molecule is different from each other antibody molecule in the mixture by about 0.5 to about 1.0 unit on the Kyte & Doolittle hydropathy scale. In certain other embodiments, each of the antibody molecules, when run alone on HIC-HPLC, elutes at a distinct run time with little overlap from the other antibody molecules in the mixture. In certain embodiments, the mixture comprises a plurality of antibody molecules (e.g., two, three, four, or five antibody molecules).

If two antibody molecules from the mixture, when run on HIC-HPLC, have significant overlap in the chromatograph monitoring elution profiles of the antibody molecules by absorbance verses time of elution, this indicates that the two antibody molecules elute at times that are close, resulting in a lack of separation within the column such that the antibody molecules are not purified (e.g., less than 50% pure). In such cases, the individual antibodies cannot be fully quantitated because of that significant overlap. In some embodiments, two antibody molecules from the mixture, when run on HIC-HPLC, have little to no overlap in the chromatograph monitoring elution profiles of the antibody molecules by absorbance verses time of elution, in that the antibody molecules elute at times that are not close, resulting in a separation such that the antibody molecules are substantially purified, each being at least 90%, 91%, 92%, 93%, 94%, 95%, 96%, 97%, 98%, 99%, or 100% pure.

In some embodiments, methods disclosed herein are used to quantitate an individual population of antibodies, also referred to as "an antibody molecule," from a mixture of antibodies, which includes two or more different populations of antibodies, where the different populations have at least one amino-acid difference between them. In some embodiments, a population of antibodies may have the same amino acid sequence as that of another population in the mixture of antibodies, but they may differ in post-translational modifications. In certain embodiments, a mixture is a co-formulated composition, such as or including a co-formulated drug substance (cFDS). In certain embodiments, a mixture comprises excipients. In certain embodiments, a mixture comprises sucrose, and may be a sucrose drug substance comprising mAb molecules. Each antibody in the mixture of antibodies will have a similar molecular weight, within 1, 2, 3, 4, 5, 10, or 15 kilodaltons (kDa) of each other. In another aspect, the average molecular weight of all the antibodies will be about 150 kDa. This method can also be used with two or more trap molecules that have similar molecular weights. In certain further embodiments, the co-formulated composition comprises VEGF-Trap. (See, e.g., U.S. Pat. No. 9,265,827 and U.S. patent application Ser. No. 14/943,490, which are incorporated by reference here in their entireties.) This method may also be used to monitor the concentration for each of the mAbs in a mixture (e.g., a co-formulation) in monitoring storage stability. In certain embodiments, this method is used to separate antibody molecules that cannot be separated by another chromatographic method, such as by reverse phase high pressure liquid chromatography (HPLC) or ultra high pressure liquid chromatography (UPLC).

Hydrophobic Interaction Chromatography (HIC) separates antibodies in a decreasing salt gradient, based on differences in surface hydrophobicity of the antibodies. Separation using HIC is based on the reversible interaction between an antibody and the hydrophobic ligand bound to the chromatography matrix. Though hydrophobic amino acids of proteins and peptides are usually located away from molecular surfaces, biomolecules have some hydrophobic groups that are exposed to allow interaction with hydrophobic ligands on media. The hydrophobic interaction is enhanced by buffers with high ionic strength.

Any suitable HIC-HPLC column may be employed for methods disclosed herein, including, without limitation, Dionex ProPac HIC-10, mAbPac HIC-10, mAbPac HIC-20, mAbPac HIC-Butyl (Dionex, Thermo Fisher Scientific, Sunnyvile, CA). The buffer may be any suitable buffer. In certain embodiments, the HIC-HPLC is performed in a buffer pH between about pH 5.0 to about pH 7.0, or between about pH 6.0 to about pH 7.0, or between about 6.5 to about 7.5. In certain embodiments, the columns are Dionex MabPac HIC-10 (100×4.6 mm, 5 μm, Pore Size 1000 A°) and ProPac HIC-10 (100×4.6 mm, 5 μm, Pore Size 300 A°).

A mixture comprising two or more antibodies is run on HIC-HPLC. The antibodies are eluted at separate times (run times). The antibodies are monitored by measuring their absorbance at, e.g., 280 nm on the UV spectrum. A chromatograph may be used to monitor and to document the run. In certain embodiments, buffers used in the HIC-HPLC are different gradients of 1M ammonium sulfate (from 100% to 0%) in 100 mM phosphate buffer.

In certain embodiments, the antibody molecules are quantitated by comparing their absorbance at 280 nm to a standard curve. A standard curve may be constructed by determining the absorbance of a known antibody at known concentrations from a HIC-HPLC run, at an absorbance of, for example, 280 nm. The greater the absorbance (or "optical density"), the higher the protein concentration. These data for known concentrations of an antibody are used to make the standard curve, plotting concentration on the X axis, and the absorbance obtained from the chromatograph of the elution profile of the antibody from the HIC-HPLC run on the Y axis. A sample comprising two or more antibodies of unknown concentrations, including the antibody from the standard curve, are run. To analyze the data, the antibodies are separated by HIC-HPLC. The elution profiles of the antibodies are displayed on a chromatograph, with antibody concentration represented by absorbance monitored over time by a spectrophotometer. The absorbance of each antibody, as identified by its elution time (run time) is used to locate a corresponding absorbance value on the standard curve. The corresponding X-axis value for that point on the standard curve is the concentration of that antibody in the sample.

In some aspects of the current disclosure, methods for quantitating individual antibodies in a mixture disclosed herein may be useful if the relative surface hydrophobicity of each antibody in the mixture is different from that of each other antibody in the mixture by greater than about 0.25 units, such as by about 0.5 to about 1.0 units, on the Kyte & Doolittle hydropathy scale. The relative surface hydrophobicity of the antibodies may be determined/estimated by a number of methods.

For example, HIC-HPLC may be used to determine the relative surface hydrophobicity of different antibody molecules. Each of the antibody molecules is run alone on HIC-HPLC and the run time (elution time) for each antibody is determined.

In certain embodiments, the difference in surface hydrophobicity between antibodies in a mixture is determined by one or more of the following methods: calculated surface hydrophobicity based on protein structure or structural model, rapid screening method for solubility in ammonium sulfate or PEG8000, and rapid screening for molecule interaction by affinity capture—self-interaction nanoparticle spectroscopy (AC-SINS).

The relative surface hydrophobicity may be calculated based on known structure of the antibody (based on, for example, crystal structure or NMR structure) or a structural model. Such computational methods are known in the art.

The relative surface hydrophobicity may be calculated/estimated by determining the solubility of the antibody molecules by, for example, rapid screening method for solubility in conditions that enhance hydrophobicity, such as in ammonium sulfate or PEG8000. The more soluble a protein, the less hydrophobic. (See, e.g., Kramer et al., Biophysical Journal Volume 12 Apr. 1907-1915 (2012).)

The relative surface hydrophobicity may be calculated/estimated by rapid screening for molecule interaction by affinity capture—self-interaction nanoparticle spectroscopy (AC-SINS). (See, e.g., Estep et al., *mAbs*, 7:3, 553-561 (2015).) AC-SINS is an approach that coats gold nanoparticles with polyclonal anti-human antibodies, uses these conjugates to immobilize human mAbs, and evaluates mAb self-interactions by measuring the plasmon wavelengths of the antibody conjugates as a function of ammonium sulfate concentration.

In certain other embodiments, antibodies in a mixture that can be separated using the described methods will have similar size or overall charge as determined by one or more of the following methods: protein structure, or structural modeling, based on sequence and other known protein structures, calculated overall protein charge property based on protein sequences, calculated hydrophobicity based on protein sequences, and protein sequencing.

In certain embodiments, antibodies in a mixture have at least 80%, at least 85%, at least 90%, at least 95%, at least 98%, or at least 99% homologous protein structure or structural models based on sequence and other known protein structures. In certain embodiments, antibodies in a mixture have calculated protein charge properties within 3, 4, or 5, 10 or 15 elementary units of one another, where protein charge properties are calculated based on protein sequence. In certain embodiments, two or more antibodies in a mixture have at least 80%, at least 85%, at least 90%, at least 95%, at least 98%, or at least 99% identity between their protein sequences.

In an aspect, methods of quantifying antibodies in a mixture using HIC-HPLC as disclosed herein may not be as useful if there is a large difference between the antibody molecules as calculated or estimated by protein structure, sequence-based structural models, protein sequence, and other known aspects of protein structure. If there are differences in the hydrophobic profiles of the antibodies, then methods using HIC-HPLC may nevertheless facilitate separation of the antibody species.

In another aspect, methods of quantifying antibodies in a mixture using HIC-HPLC as disclosed herein may not be as useful if there is a large difference between the antibody molecules calculated/estimated by the calculated overall protein charge property of each antibody molecule, based on the protein sequence of each antibody molecule. If there are differences in the hydrophobic profiles of the antibodies, then methods using HIC-HPLC may nevertheless facilitate separation of the antibody species.

In another aspect, methods of quantifying antibodies in a mixture using HIC-HPLC as disclosed herein may not be as useful if there are large differences between the antibody molecules calculated/estimated by inspecting the protein charge or size. If there are differences in the hydrophobic profiles of the antibodies, then methods using HIC-HPLC may nevertheless facilitate separation of the antibody species.

In certain embodiments, one or more of the antibodies in a mixture of antibodies are monoclonal antibodies. In certain embodiments, one or more of the monoclonal antibodies are human monoclonal antibodies. In certain embodiments, two or more of the antibody molecules are of the same isotype. In certain embodiments, two or more of the antibody molecules are variants of each other. In yet certain other embodiments, two or more of the antibody molecules bind to the same antigen. The mAbs may be whole antibody molecules.

In certain embodiments, the mixture is a co-formulated composition. In certain further embodiments, the co-formulated composition comprises two or more mAbs that are effective for treating Middle East Respiratory Syndrome (MERS) in a human patient. Antibodies to the MERS corona virus (MERS-CoV) are disclosed in, for example, U.S. patent application Ser. No. 14/717,760 and International Application Publication No. WO2015/179535A1. In certain further embodiments, the co-formulated composition comprises mAbs that are effective in treating Ebola hemorrhagic fever in a human patient. Antibodies to the Ebola virus are disclosed in, for example, U.S. patent application Ser. No. 15/005,334, filed on Jan. 25, 2016. In certain further embodiments, the co-formulated composition comprises mAbs that are effective in treating macular degeneration in a human patient. In certain further embodiments, the co-formulated composition comprises mAbs alirocumab and evinacumab disclosed in U.S. Provisional Application No. 62/302,907. In certain embodiments, the co-formulated composition comprises PD1 antibodies and other immune-oncology antibody products, such as bispecific antibodies.

(See, e.g., disclosure of PD-1 and CD3×CD20 in U.S. Provisional Application No. 62/270,749, U.S. patent application Ser. No. 15/386,443, and U.S. patent application Ser. No. 15/386,453; and PD-1 and Lag3 in U.S. Provisional Application 62/365,006 and U.S. patent application Ser. No. 15/289,032.) In certain embodiments, the co-formulated composition comprises anti-Zika virus antibodies. (See, e.g., U.S. Provisional Application No. 62/363,546.) In certain further embodiments, the co-formulated composition comprises trevogrumab and Activin A antibodies. (See, e.g., U.S. Pat. No. 8,871,209.) In certain embodiments, two or more antibodies in the co-formulated composition may treat an infectious disease in a human patient. The disclosure of each of the above-cited patent documents in this paragraph is hereby incorporated by reference.

The anti-MERS mAbs in a co-formulation may bind to, for example, the spike protein of MERS-CoV (e.g., the spike protein of MERS-CoV isolate EMC/2012). The spike protein's epitope may be within the receptor binding domain of the spike protein (e.g., amino acids selected from the amino acids 367 to 606 of GenBank Accession No. AFS88936.1). The anti-MERS mAbs in the co-formulated composition may be: a fully human monoclonal antibody that binds to the MERS-CoV spike protein; one that interacts with one or more amino acid residues in the receptor binding domain of the MERS-CoV spike protein selected from amino acid residues 367 to 606 of GenBank Accession No. AFS88936.1; one that binds to MERS-CoV spike protein with a dissociation constant (Ko) of less than 18.5 nM, as measured in a surface plasmon resonance assay; or one that blocks binding of MERS-CoV spike protein to dipeptidyl peptidase 4 (DPP4) by more than 90%.

The co-formulated composition may be any composition comprising two or more antibodies directed to the same or different target, and are effective in treating the same or different disease or condition in a patient, including a human patient.

Pharmaceutical Compositions and Formulations

Compositions containing two or more antibody molecules may be formulated as a pharmaceutical composition (e.g., a DP) for administering to a subject. The pharmaceutical compositions can include, for example, three antibody molecules. Any suitable pharmaceutical compositions and formulations, as well as suitable methods for formulating and suitable routes and suitable sites of administration, are within the scope of this invention. Also, unless otherwise stated, any suitable dosage(s) and frequency of administration are contemplated.

The mAbs in the co-formulations are purified by methods known in the art before being co-administered. The co-formulations of two or more antibodies may be any suitable co-formulations.

The pharmaceutical compositions/co-formulations may include a pharmaceutically acceptable carrier (i.e., an excipient). A "pharmaceutically acceptable carrier" refers to, and includes, any and all solvents, dispersion media, coatings, antibacterial and antifungal agents, isotonic and absorption delaying agents, diluents, glidants, etc. The compositions can include a pharmaceutically acceptable salt, e.g., an acid addition salt or a base addition salt (see e.g., Berge et al. *J Pharm Sci* 66:1-19 (1977)). The composition can include sucrose or can be coated when appropriate.

In certain embodiments, the protein compositions can be stabilized and formulated as a solution, microemulsion, dispersion, liposome, lyophilized cake, solid, etc. Sterile injectable solutions can be prepared by incorporating two or more mAbs in the required amounts in an appropriate solvent with one or a combination of ingredients enumerated above, as required, followed by filtered sterilization. Generally, dispersions are prepared by incorporating two or more mAb molecules into a sterile vehicle that contains a basic dispersion medium and the required other ingredients from those enumerated above. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

EXAMPLES

For this invention to be better understood, the following examples are set forth. These examples are for purposes of illustration only and are not be construed as limiting the scope of the invention in any manner.

The anti-Ebola mAbs in the co-formulation used in Examples 1 and 3-7 are whole, fully human IgG 1 monoclonal antibodies. The three mAbs (mAb A, mAb B, and mAb C) have similar molecular weights (e.g., about 145 kDa), protein structure, and charge properties (e.g., a difference in pI of about 0.6 or less, as determined by protein sequences). The isoelectric point (pI) of mAb A is determined to be 9.0, the pI of mAb B is determined to be 8.5, and the pI of mAb C is determined to be 9.1.

The anti-MERS mAbs in the co-formulation used in Example 2 are whole, fully human anti-Ebola mAbs. The two mAbs have similar molecular weights (e.g., within about 15 kDa of one another) and charge properties. (See U.S. Patent Publication No. US2015/0337029, WO2015/179535A1, and U.S. patent application Ser. No. 14/717,760, the disclosure of each of which is hereby incorporated by reference herein.)

Example 1

A HIC-HPLC method is used to quantitate 3 anti-Ebola monoclonal antibodies (mAb 1, mAb 2, and mAb 3) of similar molecular weights, protein structures, and charge properties from a co-formulation by first separating the 3 mAbs from the co-formulation and then quantitating each of them.

A Dionex ProPac HIC-10 column is used, Cat #063655 (Dionex, Thermo Fisher Scientific, Sunnyville, CA), 4.6× 100 mm.

Preparation of Mobile Phases

The mobile phases include a Mobile Phase A and a Mobile Phase B. Mobile Phase A includes 1M Ammonia phosphate and 100 mM phosphate, at a pH of 7.0. Preparation of Mobile Phase A includes: dissolving 13.8 g of sodium phosphate monobasic, monohydrate ($NaH_2PO_4 \cdot H_2O$) and 132.1 g of ammonia phosphate in 800 mL Milli Q; adjusting the pH to 7.0 with 50% NaOH; bringing the volume to 1000 mL; and filtering the solution through a 0.22 µM filter. Mobile Phase B includes 100 mM phosphate at a pH of 7.0. Preparation of Mobile Phase B includes: Dissolving 13.8 g of sodium phosphate monobasic, monohydrate ($NaH_2PO_4 \cdot H_2O$) in 900 mL Milli Q; adjusting the pH to 7.0 with 50% NaOH; bringing the volume to 1000 mL; and filtering the solution through a 0.22 µM filter.

HIC-HPLC Method

The HIC-HPLC is run through the aforementioned column at a flow rate of 0.5 mL/minute. The column temperature is kept at 30° C., and the co-formulation sample temperature is 5° C. The stop time for the column is 40 minutes. The effluent's absorbance of 280 nm ultraviolet light is monitored using a UV detector. Table 1 below shows the mix of Mobile Phase A and Mobile Phase B as percentages of the mobile phase composition gradient to be introduced over the column run time.

TABLE 1

Mobile phase gradient

| Time (min) | % Mobile Phase A | % Mobile Phase B |
|---|---|---|
| 0 | 60 | 40 |
| 4 | 60 | 40 |
| 19 | 0 | 100 |
| 32 | 0 | 100 |
| 33 | 60 | 40 |
| 40 | 60 | 40 |

Calibration with Three Individual mAbs

In order to calibrate results for the three individual mAbs, known amounts of each mAb in FDS are run. A FDS with a known concentration of each mAb is prepared, and the concentration is measured by either reverse phase (RP) chromatography or Solo VPE® Spectroscopy (e.g., C Technologies, Inc.). The known FDS for each mAb are as follows:

TABLE 2

Concentration of each mAb FDS as measured by RP or Solo VPE ®

| Formulation | Known mAb amount (g) | Known mAb concentration (t = 0) (mg/mL) |
|---|---|---|
| mAb 1 FDS | 84.08 | 51.31 (by Solo VPE ®) |
| mAb 2 FDS | 84.13 | 53.40 (by RP) |
| mAb 3 FDS | 84.19 | 50.65 (by RP) |

A control sample is also prepared for the calibration sequence. The control sequence has a concentration of 50.31 mg/mL as measured by Solo VPE® Spectroscopy (e.g., C Technologies, Inc.). One injection of the control sample is 12.0 µL (603.72 µg).

Table 2 below lists the calibration samples used of each of the mAb FDS.

TABLE 2

Calibration samples

| Amount | Number of injections |
|---|---|
| mAb 1 FDS: 50.5 mg/mL working Standard Lot # YC10190-42A (Regeneron Pharmaceuticals, Tarrytown, NY) | |
| 2.0 µL = 101 µg | 1 injection |
| 3.0 µL = 151.5 µg | 1 injection |
| 4.0 µL = 201 µg | 1 injection |
| 5.0 µL = 252.5 µg | 1 injection |
| 6.0 µL = 303 µg | 1 injection |
| mAb 2 FDS: 51.7 mg/mL working Standard Lot # YC10190-42B (Regeneron Pharmaceuticals, Tarrytown, NY) | |
| 2.0 µL = 103.4 µg | 1 injection |
| 3.0 µL = 155.1 µg | 1 injection |
| 4.0 µL = 206.8 µg | 1 injection |
| 5.0 µL = 258.5 µg | 1 injection |
| 6.0 µL = 310.2 µg | 1 injection |
| mAb 3 FDS: 51.4 mg/mL working Standard Lot # YC10190-42C (Regeneron Pharmaceuticals, Tarrytown, NY) | |
| 2.0 µL = 102.8 µg | 1 injection |
| 3.0 µL = 154.2 µg | 1 injection |
| 4.0 µL = 205.6 µg | 1 injection |
| 5.0 µL = 257 µg | 1 injection |
| 6.0 µL = 308.4 µg | 1 injection |

The calibration sequence is run. During the calibration sequence, one injection of the control sample is introduced at the beginning of each sample set (e.g., the set of mAb 1 FDS injections, the set of mAb 2 FDS injections, or the set of mAb 3 FDS injections), after every 20-24 injections of mAb FDS, and at the end of each injection sequence.

During one calibration sequence, one injection of each known amount of mAb is performed. During another calibration sequence, four injections of each known amount of mAb are performed to determine repeatability of injections.

A standard calibration curve is constructed for each mAb. The calibration curve for each mAb has an $R^2 \geq 0.999$, and the variability of repeated injections of the same amounts of each mAb is 1%.

Control Specifications

A control HIC-HPLC run of each known mAb FDS is performed. Percent recovery for each known mAb FDS is calculated by measuring the concentration by HIC-HPLC, and then dividing the concentration measured by HIC-HPLC by the known mAb concentration in Table 2. Percent recovery is calculated to be 90-110% of the known concentrations for all three known mAb FDS.

Unknown Samples

A sample co-formulation having a total of 600 µg mAb (e.g., 12 µL of a 50 mg/mL mAb sample) is run through HIC-HPLC. For example, 12 µL of a co-formulation including 600 µg total of mAb may include the equivalent of three injections of 200 µg/injection of individual mAb. The individual mAbs in the co-formulation are mAb 1, mAb 2, and mAb 3.

A duplicate run of the sample is performed, and the average concentration (mg/mL) of each individual mAb in the co-formulation and the ratio of each mAb to the total amount of mAb is reported.

FIG. 1 is a chromatograph showing an HIC-HPLC run of this co-formulation. Each mAb is depicted by a separate line, and the cFDS as a whole is also depicted by a line. The 3 antibodies are well separated by HIC-HPLC, with little overlap in peaks.

Example 2

Multiple HIC-HPLC methods are used to quantitate 2 anti-MERS monoclonal antibodies of similar molecular weights and charge properties from a co-formulation by first separating the 2 mAbs from the co-formulation and then quantitating each of them.

mAb Drug Substances

Two mAb (mAb 1 and mAb 2) drug substances are combined. mAb 1 drug substance includes 52.3 mg/ml mAb 1 and 10 mM His, at a pH of 5.5 (Regeneron Pharmaceuticals, Tarrytown, NY). mAb 2 drug substance includes 40.4 mg/ml mAb 2 and His, at a pH of 6.0, and includes 5% (w/v) sucrose (Regeneron Pharmaceuticals, Tarrytown, NY).

HIC-HPLC Methods

Seven HIC-HPLC methods are run. In each method, 50 μg (mAb 1 and mAb 2) of sample is loaded. The effluent is monitored using UV detection at 280 nm. Two solvents are used, in varying proportion, in the mobile phase. Solvent A is 1M $(NH_4)SO_4$ 20 mM Acetate at pH 5.5, and Solvent B is 20 mM Acetatae at pH 5.5.

1. Method 1

TABLE 3.1

| | Method 1 gradient and flow information | | |
|---|---|---|---|
| Time (min) | Flow (mL/min) | % A in mobile phase | % B in mobile phase |
| Startup | 0.500 | 100 | 0 |
| 4 | 0.500 | 100 | 0 |
| 29 | 0.500 | 0 | 100 |
| 40 | 0.500 | 0 | 100 |
| 41 | 0.500 | 100 | 0 |
| 50 | 0.500 | 100 | 0 |

Figure 2:
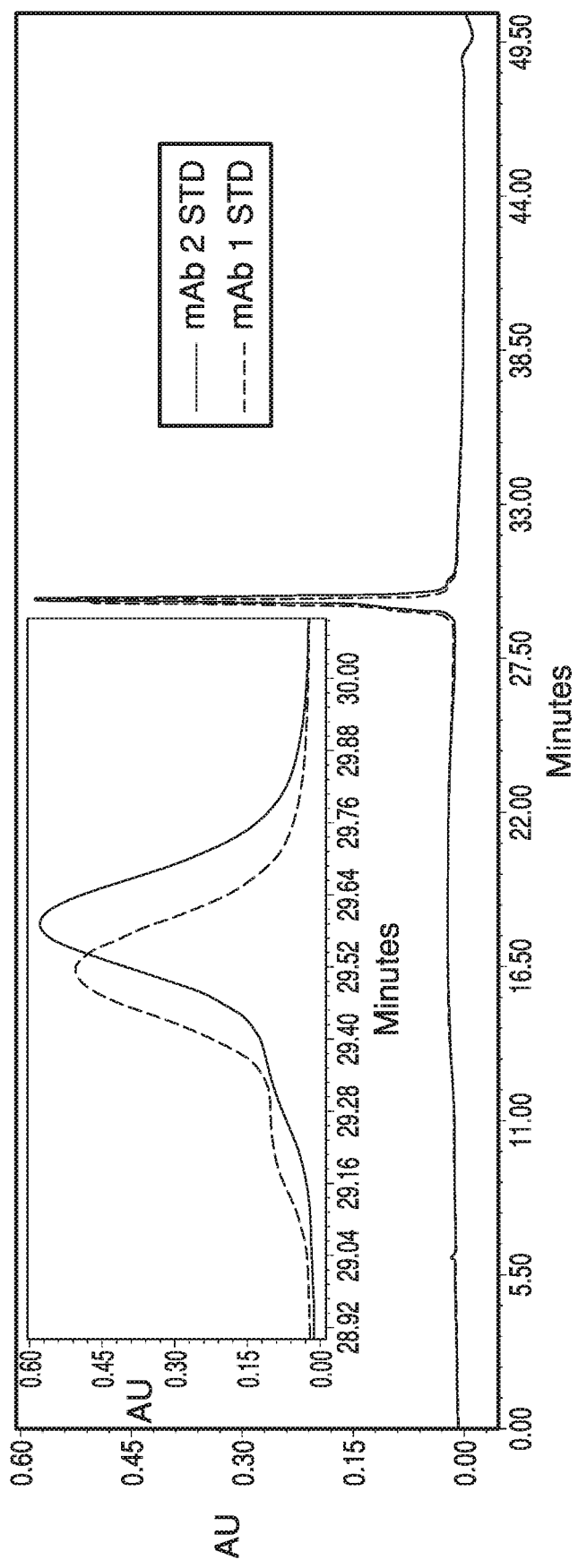
FIGS. 2-8 show exemplary chromatographs of HIC-HPLC runs of a co-formulation comprising anti-MERS mAbs.

FIG. 2 shows a chromatograph of this run. The two antibodies are somewhat separated but have significant overlap.

2. Method 2—0.5% Per Minute

TABLE 3.2

| | Method 2 gradient and flow information | | |
|---|---|---|---|
| Time (min) | Flow (mL/min) | % A in mobile phase | % B in mobile phase |
| Startup | 0.500 | 40 | 60 |
| 4 | 0.500 | 40 | 60 |
| 40 | 0.500 | 20 | 80 |
| 41 | 0.500 | 0 | 100 |
| 51 | 0.500 | 0 | 100 |
| 52 | 0.500 | 40 | 60 |
| 56 | 0.500 | 40 | 60 |

Figure 3:
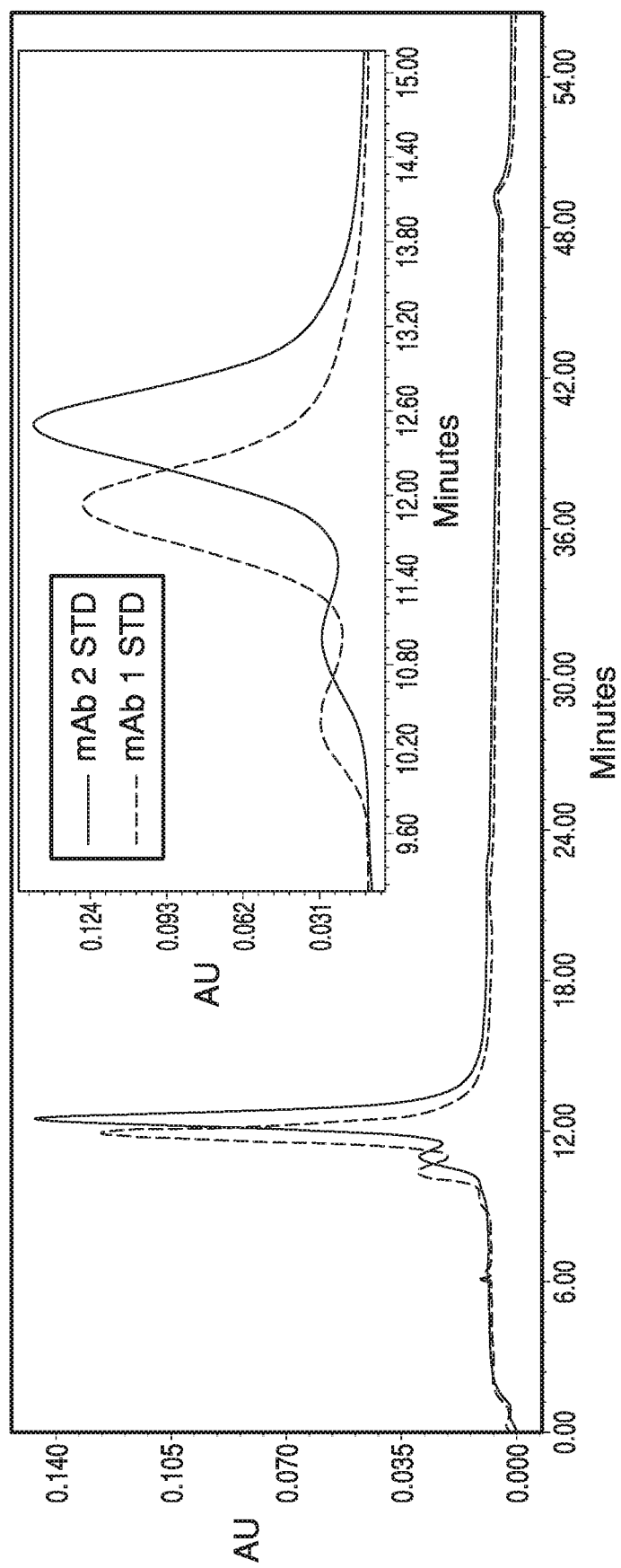

FIG. 3 shows a chromatograph of this run. The two antibodies are somewhat separated but have significant overlap.

3. Method 3—0.2% Per Minute

TABLE 3.3

| | Method 3 gradient and flow information | | |
|---|---|---|---|
| Time (min) | Flow (mL/min) | % A in mobile phase | % B in mobile phase |
| Startup | 0.500 | 39 | 61 |
| 4 | 0.500 | 39 | 61 |
| 49 | 0.500 | 39 | 70 |
| 50 | 0.500 | 0 | 100 |
| 60 | 0.500 | 0 | 100 |
| 61 | 0.500 | 39 | 61 |
| 65 | 0.500 | 39 | 61 |

Figure 4:
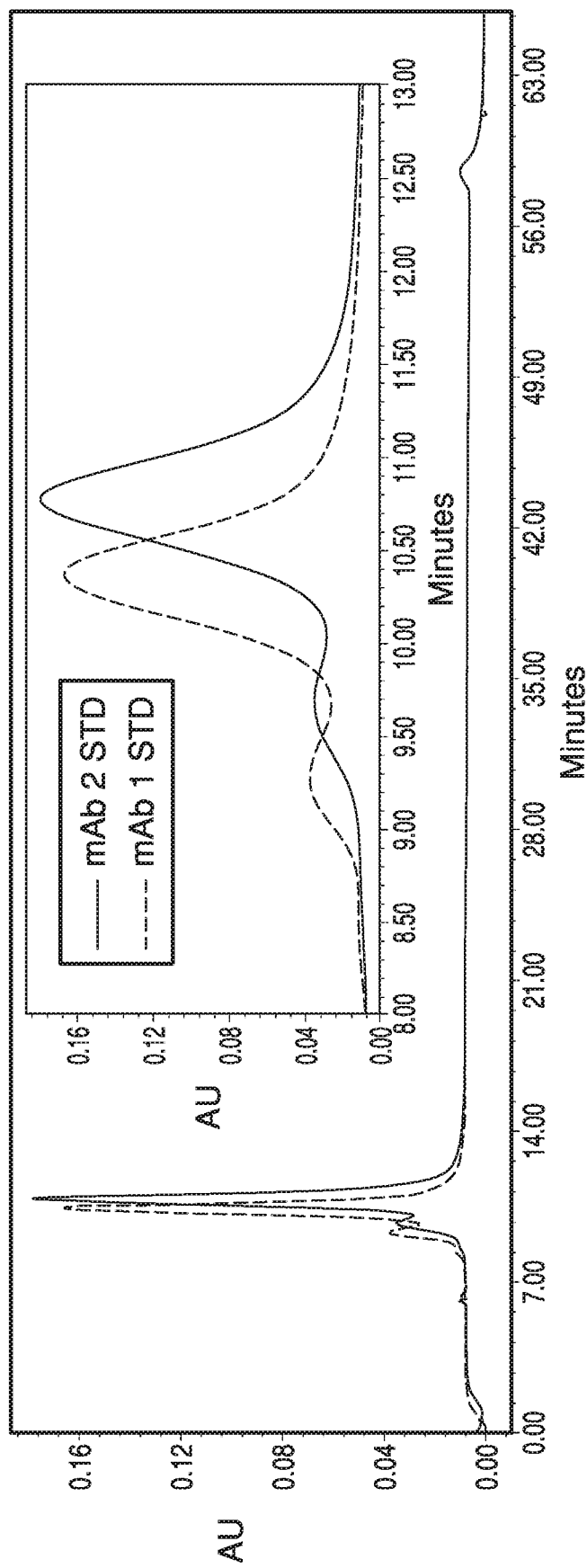

FIG. 4 shows a chromatograph of this run. The two antibodies are somewhat separated but have significant overlap.

4. Method 4—2% Per Minute

TABLE 3.4

| | Method 4 gradient and flow information | | |
|---|---|---|---|
| Time (min) | Flow (mL/min) | % A in mobile phase | % B in mobile phase |
| Startup | 0.500 | 100 | 0 |
| 4 | 0.500 | 100 | 0 |
| 34 | 0.500 | 40 | 60 |
| 35 | 0.500 | 0 | 100 |
| 45 | 0.500 | 0 | 100 |
| 46 | 0.500 | 100 | 0 |
| 50 | 0.500 | 100 | 0 |

Figure 5:
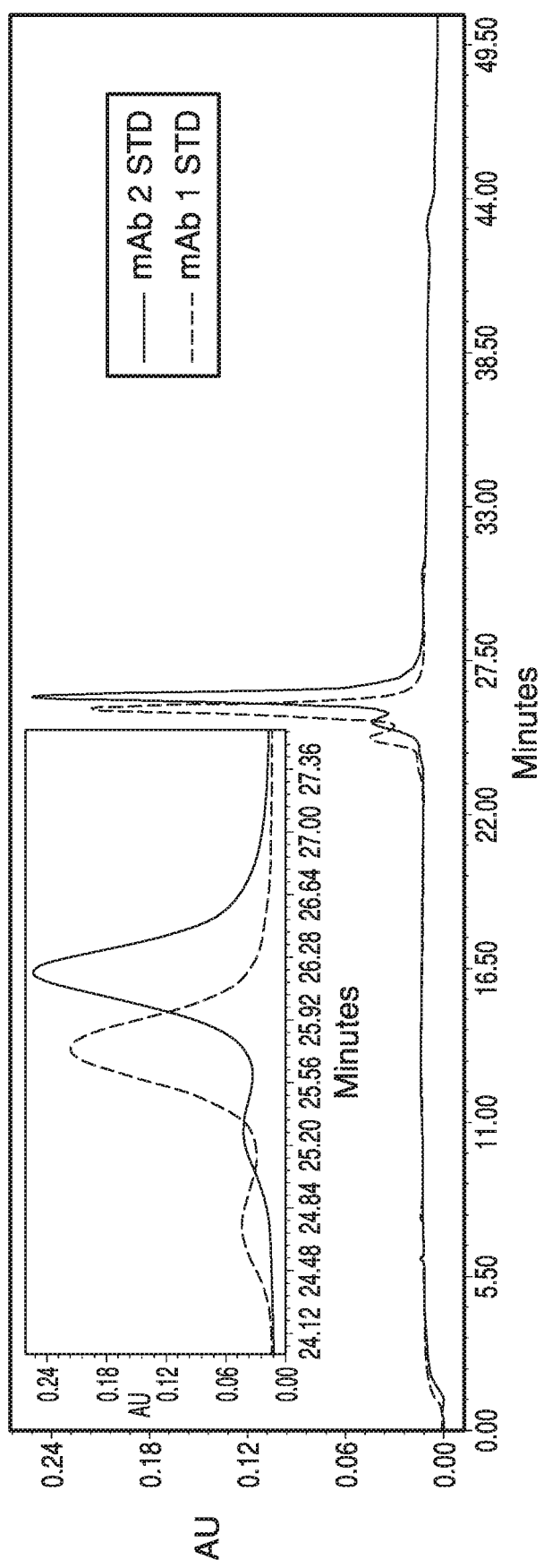

FIG. 5 shows a chromatograph of this run. The two antibodies are somewhat separated but still have some overlap.

5. Method 5—1% Per Minute

TABLE 3.5

| | Method 5 gradient and flow information | | |
|---|---|---|---|
| Time (min) | Flow (mL/min) | % A in mobile phase | % B in mobile phase |
| Startup | 0.500 | 80 | 20 |
| 4 | 0.500 | 80 | 20 |
| 34 | 0.500 | 50 | 50 |
| 35 | 0.500 | 0 | 100 |
| 45 | 0.500 | 0 | 100 |
| 46 | 0.500 | 80 | 20 |
| 50 | 0.500 | 80 | 20 |

Figure 6:
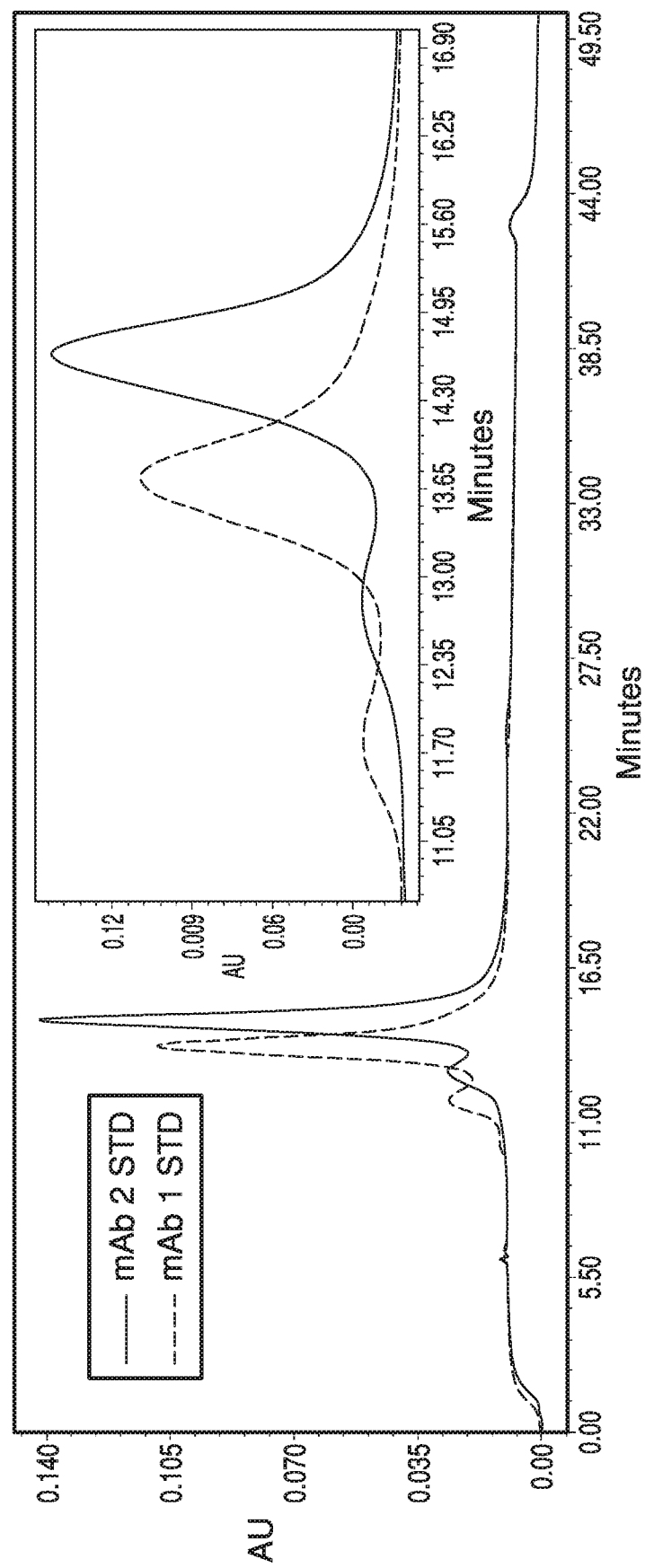

FIG. 6 shows a chromatograph of this run. The two antibodies are somewhat separated but have some overlap.

6. Method 6—1% Per Min

TABLE 3.6

| | Method 6 gradient and flow information | | |
|---|---|---|---|
| Time (min) | Flow (mL/min) | % A in mobile phase | % B in mobile phase |
| Startup | 0.500 | 90 | 10 |
| 4 | 0.500 | 90 | 10 |
| 44 | 0.500 | 50 | 50 |
| 45 | 0.500 | 0 | 100 |
| 55 | 0.500 | 0 | 100 |
| 56 | 0.500 | 90 | 10 |
| 60 | 0.500 | 90 | 10 |

Figure 7:
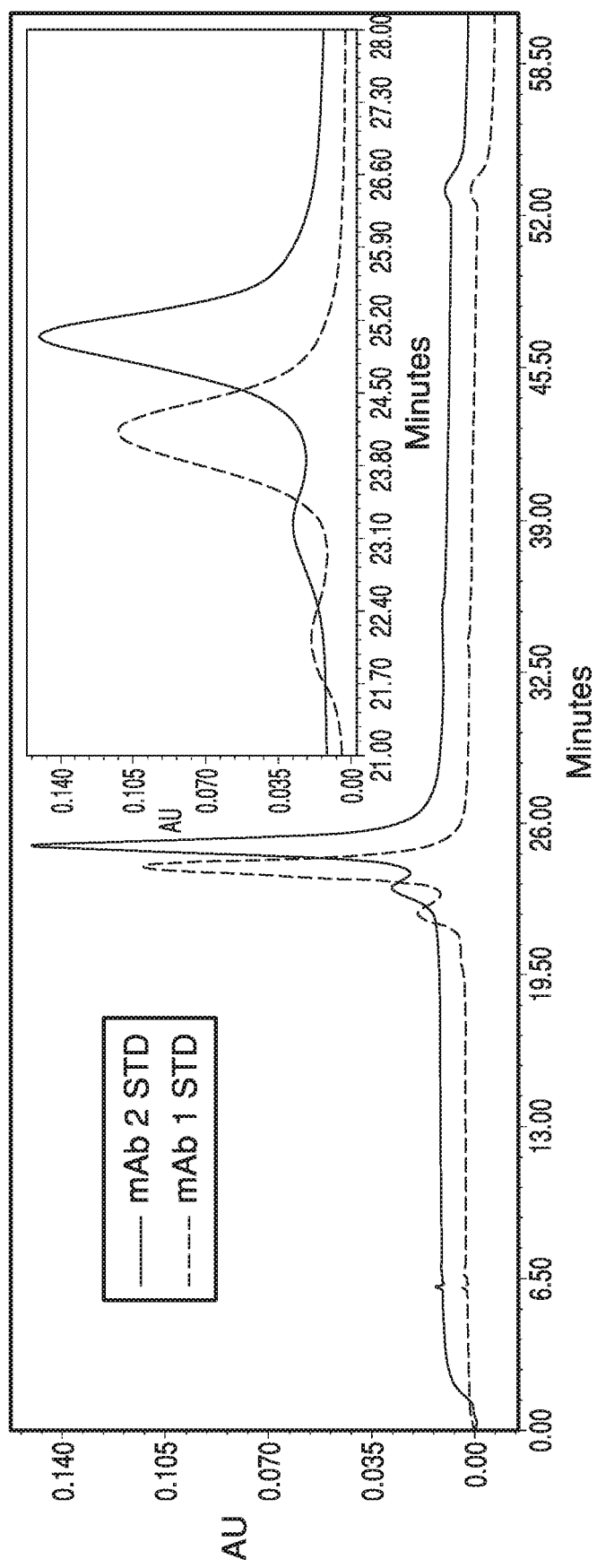

FIG. 7 shows a chromatograph of this run. The two antibodies are somewhat separated but have some overlap.

7. Method 7—0.5% Per Minute

TABLE 3.7

| | Method 7 gradient and flow information | | |
|---|---|---|---|
| Time (min) | Flow (mL/min) | % A in mobile phase | % B in mobile phase |
| Startup | 0.500 | 87 | 130 |
| 4 | 0.500 | 87 | 13 |
| 74 | 0.500 | 52 | 48 |
| 75 | 0.500 | 0 | 100 |
| 85 | 0.500 | 0 | 100 |
| 86 | 0.500 | 87 | 13 |
| 90 | 0.500 | 87 | 13 |

Figure 8:
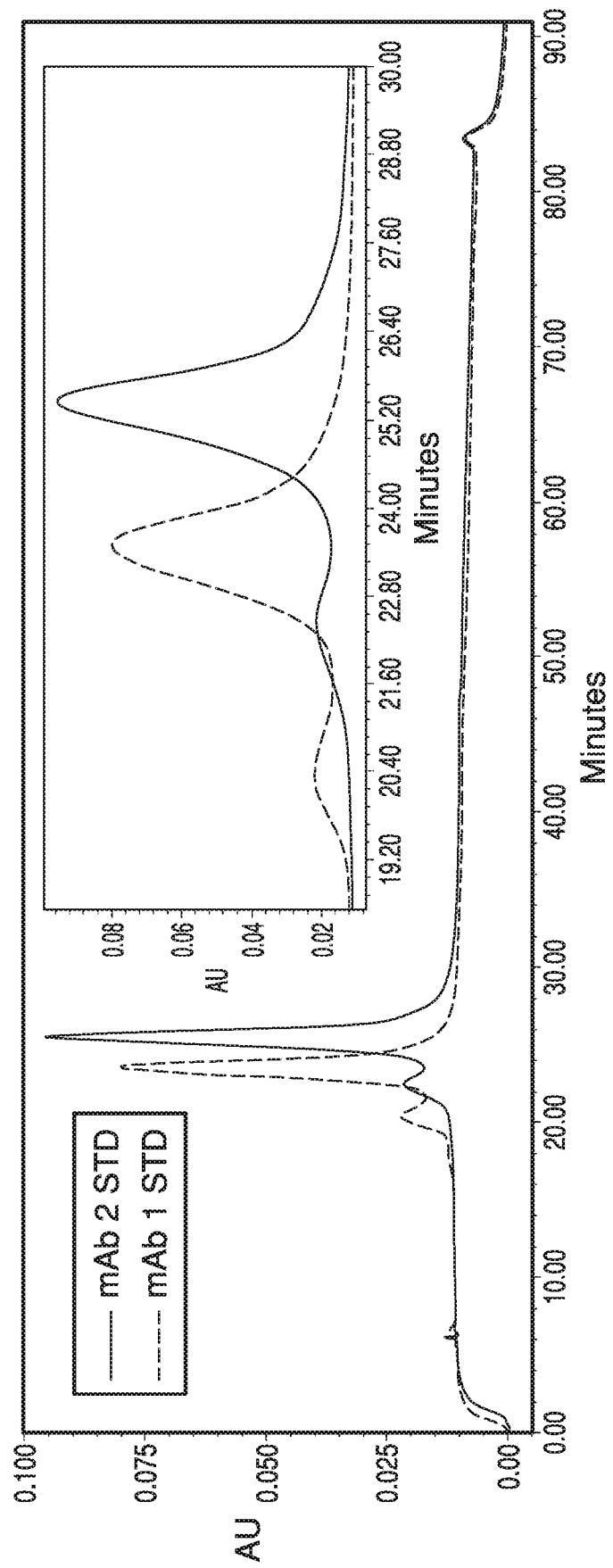

FIG. 8 shows a chromatograph of this run. The two antibodies are somewhat separated but have some overlap.

Example 3

HIC separation of a co-formulation comprising 3 anti-Ebola mAbs of similar molecular weights, protein structures, and charge properties is developed and evaluated on Agilent 1100 HPLC system.

The HIC-HPLC method uses a Dionex ProPac HIC-10 column with a two-part mobile phase (including Mobile Phase A (100 mM phosphate, 1 M ammonium sulfate, pH 7.0) and Mobile Phase B (100 mM phosphate, pH 7.0)) at a flow rate of 0.5 mL/minute. The HIC method is qualified using a five-point calibration curve for each mAb. The accuracy (% recovery) is determined by comparing the measured concentration to the theoretical concentration of each mAb. A gradient of 600 to 0 mM ammonium sulfate is used to run the column.

Figure 9:
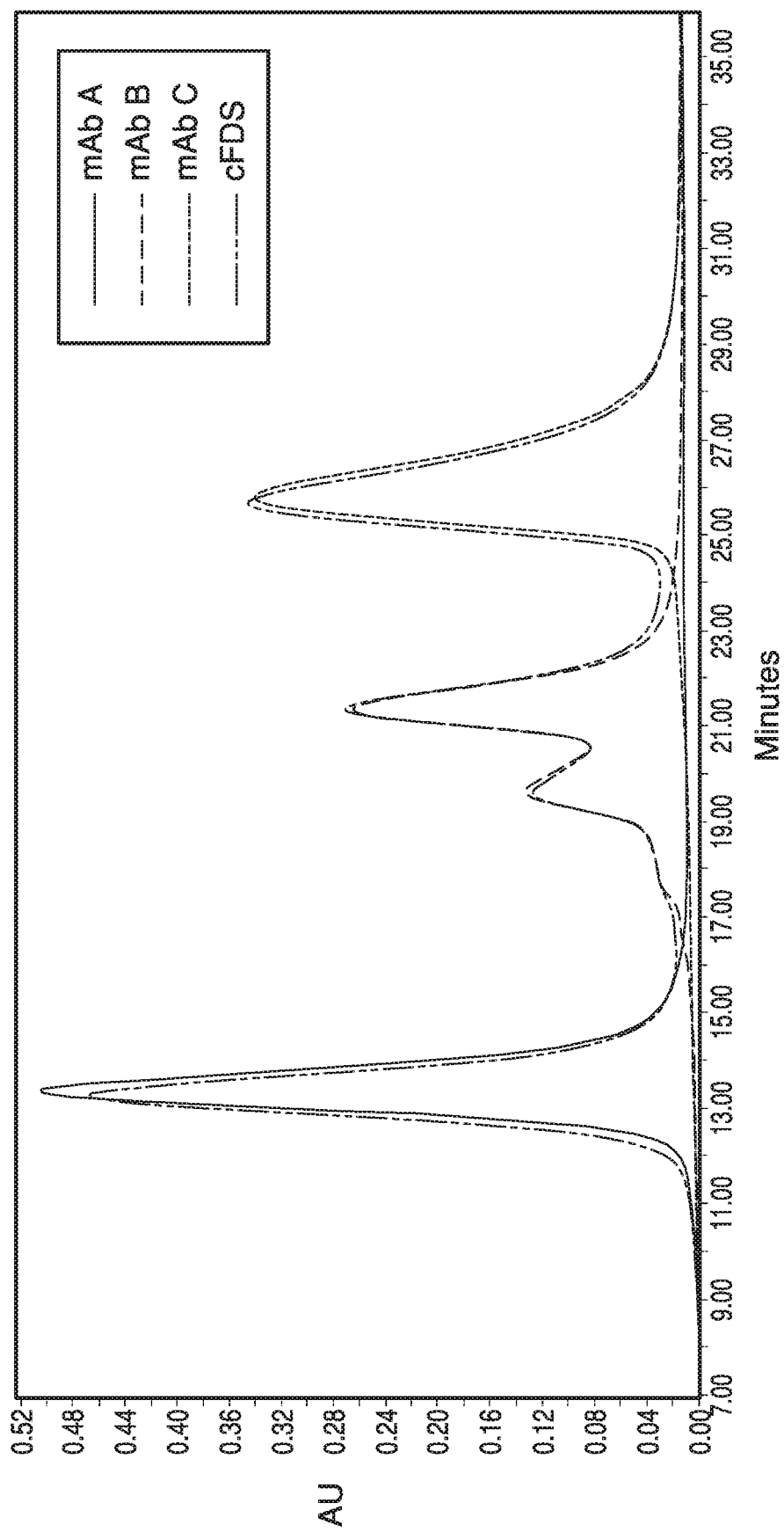
FIG. 9 shows an exemplary chromatograph of a HIC-HPLC run of a co-formulation comprising anti-Ebola mAbs.

FIG. 9 shows a chromatograph of the HIC-HPLC run. As can be seen by the three distinct peaks, the three antibodies are well separated and their peaks have little to no overlap.

Repeatability and Precision of HIC-HPLC

The repeatability is evaluated by analyzing samples of the cFDS in triplicate at 75%, 100%, 125%, 150% of the target amount (600 µg/injection of cFDS). The relative standard deviation (RSD) of repeatability is determined to be ≤0.2%.

TABLE 4

Repeatability data

| Inject amount | Measured Concentration [mg/mL] | | | | | |
|---|---|---|---|---|---|---|
| cFDS | mAb A | | mAb B | | mAb C | |
| [µg] | Ave (n = 3) | RSD | Ave (n = 3) | RSD | Ave (n = 3) | RSD |
| 450 | 17.4 | 0.1% | 17 | 0.2% | 17.9 | 0.2% |
| 600 | 17.4 | 0.1% | 17.3 | 0.1% | 17.8 | 0.2% |
| 750 | 17.3 | 0.1% | 17.4 | 0.2% | 17.7 | 0.1% |
| 900 | 17.1 | 0.1% | 17.5 | 0.1% | 17.6 | 0.2% |

The repeatability study is repeated on a different day, using a different lot of column and different batch of mobile phase. The RSD of intermediate precision is determined to be ≤1.7%.

TABLE 5

Intermediate precision

| Inject amount | Measured Concentration [mg/mL] | | | | | |
|---|---|---|---|---|---|---|
| cFDS | mAb A | | mAb B | | mAb C | |
| [µg] | Ave (n = 6) | RSD | Ave (n = 6) | RSD | Ave (n = 6) | RSD |
| 450 | 17.3 | 0.8% | 17.2 | 0.9% | 18.0 | 0.7% |
| 600 | 17.4 | 0.1% | 17.3 | 0.2% | 18.0 | 1.1% |
| 750 | 17.4 | 0.4% | 17.4 | 0.2% | 18.0 | 1.7% |
| 900 | 17.1 | 0.1% | 17.4 | 0.6% | 17.8 | 1.6% |

Linearity of HIC-HPLC

Figure 10:
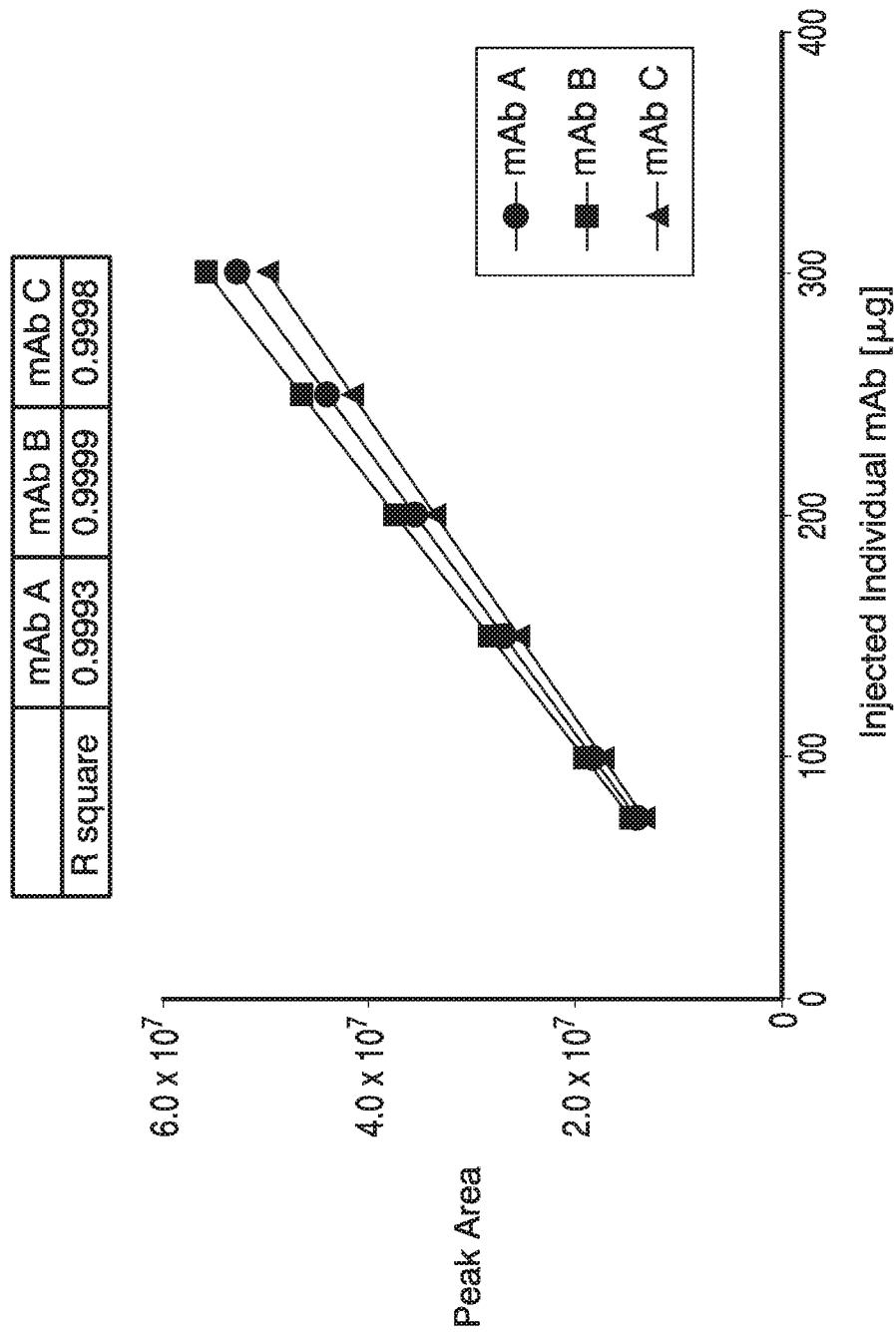
FIG. 10 is a plot of linearity of HIC-HPLC, plotting peak area against the amount of individual anti-Ebola mAb run.

Linearity is determined by analyzing samples of cFDS samples in triplicate at 9 levels (75 to 1200 µg of cFDS; 25 to 400 µg of individual mAb). A plot (FIG. 10) of the peak area of individual mAb versus the injected amount results in a linear curve: At 75 to 300 µg, $R^2 \geq 0.999$; at 25 to 400 µg, $R^2 \geq 0.98$.

Range of HIC-HPLC

Figure 11:
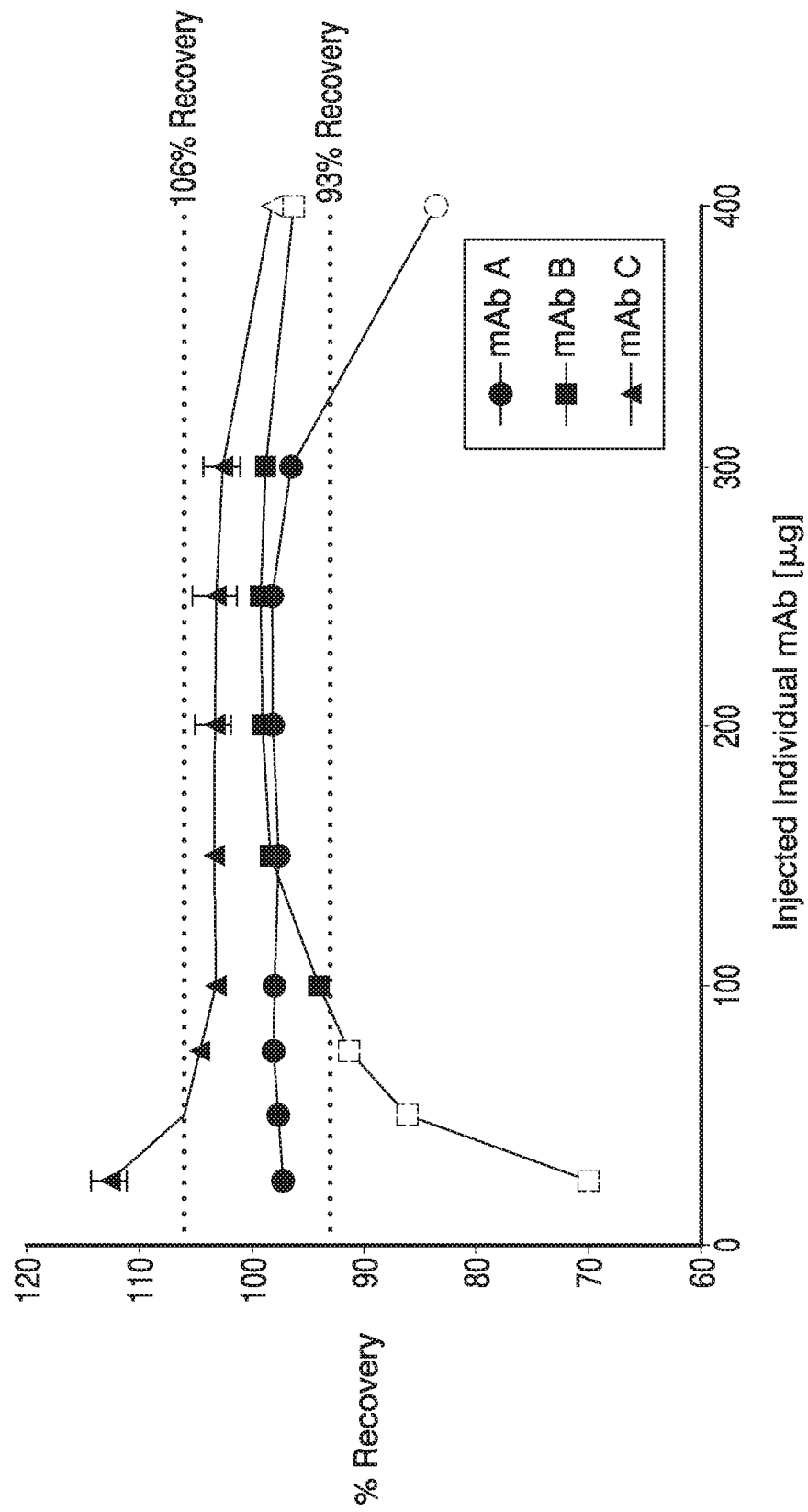
FIG. 11 is a plot of range, plotting percent recovery of the mAbs against the amount of individual anti-Ebola mAb run.

The range is the interval between the lowest and highest concentration for which the method can demonstrate acceptable precision (≤1.7%), accuracy (93-106% Recovery) and linearity ($R^2 \geq 0.999$). The range is determined to be 300 to 900 µg for cFDS sample (100 to 300 µg for each individual mAb). FIG. 11 is a plot of the % recovery of the mAbs vs. amount of individual mAb.

Accuracy of HIC-HPLC Across Different Lots of cFDS

Figure 12:
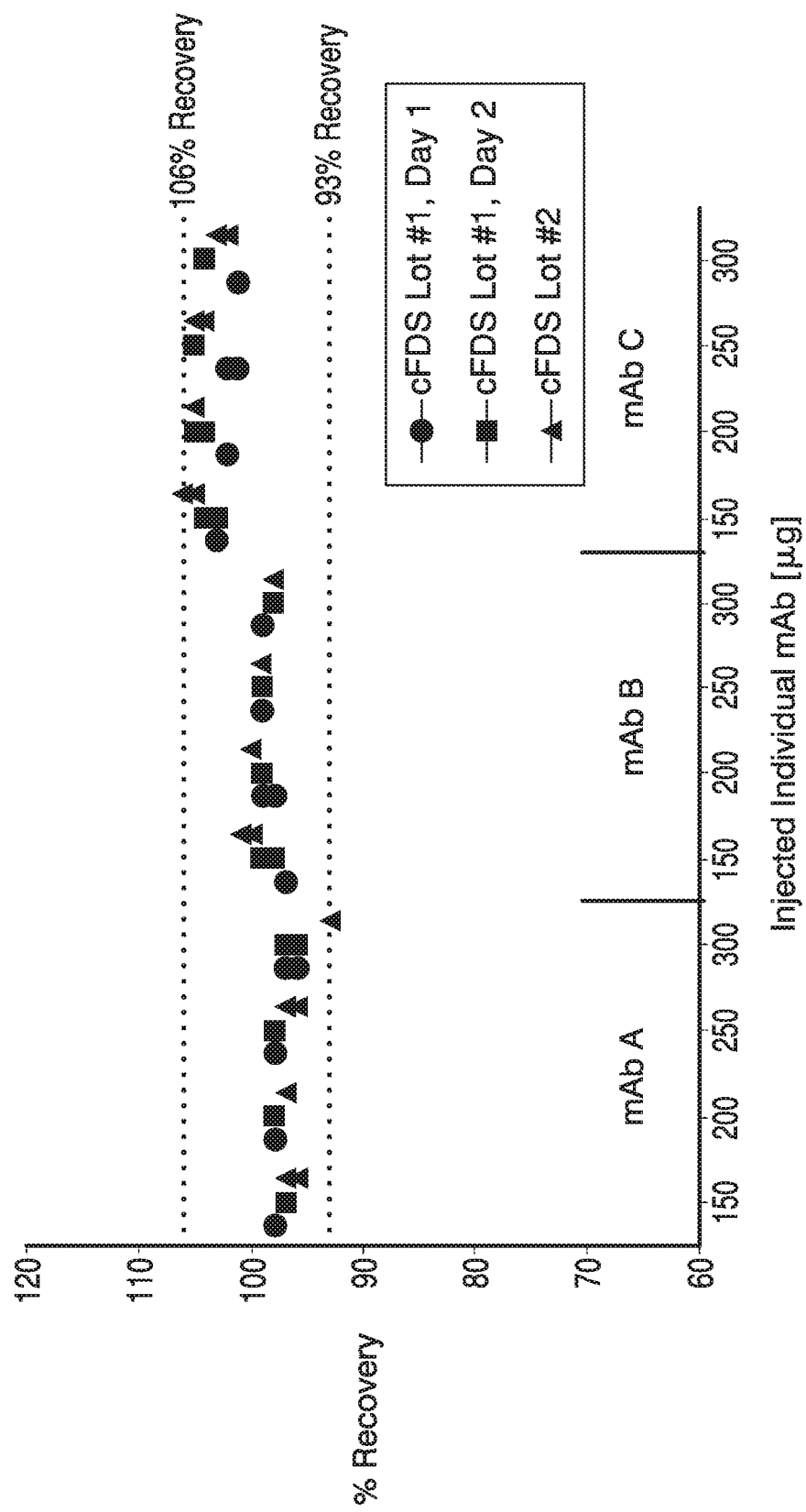
FIG. 12 is a plot of the accuracy of HIC-HPLC with different mixture sample lots, plotting percent recovery of the mAbs against the amount of individual anti-Ebola mAb run.

Data obtained from intra-day and inter-day precision (cFDS lot #1), and range study (cFDS lot #2) is used to evaluate the method accuracy. FIG. 12 is a plot of the % recovery of the mAbs vs. amount of individual mAb. % Recovery are within 93-106% at 75%, 100%, 125%, 150% of the target amount (600 µg total protein, 200 µg each mAb). The accuracy (% Recovery) is determined to be 93%-106%.

Accuracy of HIC-HPLC Across Various Ratios of Individual mAb in cFDS

Figure 13:
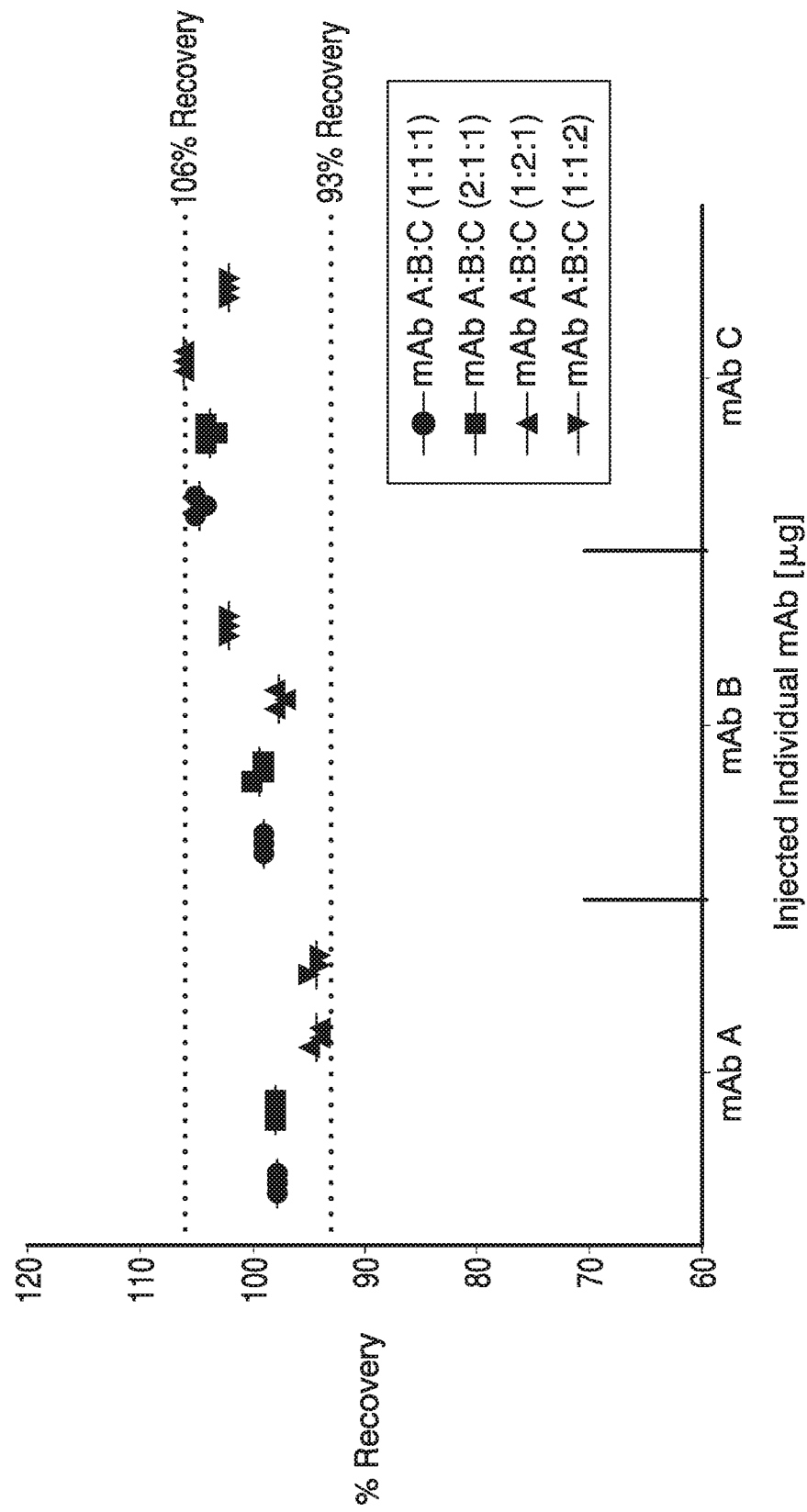
FIG. 13 is a plot of the accuracy of HIC-HPLC with different ratios of individual anti-Ebola mAbs, plotting percent recovery of the mAbs against the amount of individual anti-Ebola mAb run.

CFDS is formulated by 1:1:1, 2:1:1, 1:2:1, 1:1:2 mix of individual mAb. Each cFDS is analyzed at 100% of the target amount (600 µg/injection, n=3). FIG. 13 is the % recovery of the mAbs vs. each individual mAb in different cFDS ratios. % Recovery are within 94-106% with repeatability ≤0.3%.

TABLE 6

HIC-HPLC data summary

| Repeatability (450-900 µg cFDS) (n = 3) | mAb A | ≤0.1% |
|---|---|---|
| | mAb B | ≤0.2% |
| | mAb C | ≤0.2% |
| Intermediate Precision (450-900 µg cFDS) (n = 6) | mAb A | ≤0.8% |
| | mAb B | ≤0.9% |
| | mAb C | ≤1.7% |
| Accuracy (% Recovery) (450-900 µg cFDS) | | 93-106% |
| Linearity | | $R^2 \geq 0.999$ (a plot of the peak area of each mAb versus the injected individual mAb amount in cFDS at 75 to 300 µg range) |
| Standard Curve | | $R^2 \geq 0.999$ (50-300 µg of individual mAb standard) |
| Range | | 100 to 300 µg for each individual mAb 300 to 900 µg for cFDS sample |

Application of HIC-HPLC in Co-Formulation Development

Use of HIC-HPLC to quantitate each of the mAbs in a co-formulation or a DP may have a variety of applications in co-formulation development. For example, the concentration of each mAb in a co-formulation or a DP may be monitored in a storage stability study.

Figure 14:
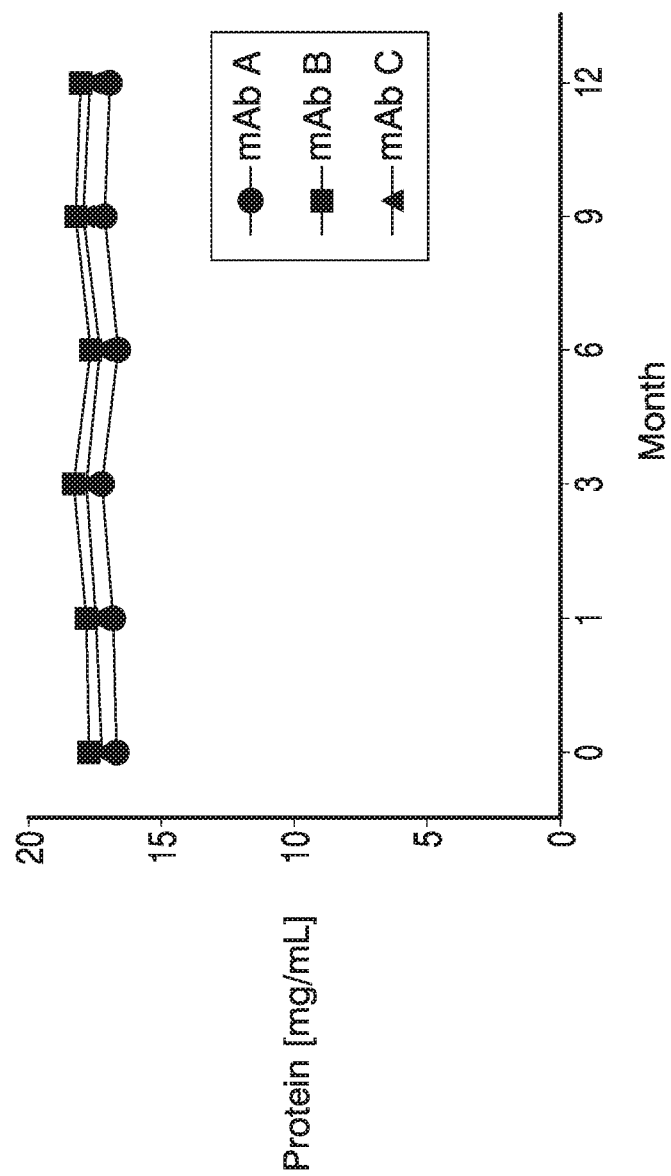
FIG. 14 is a plot of storage stability of the mAbs in the cFDS, plotting amount of individual anti-Ebola mAbs against storage time in months.

FIG. 14 shows a chart monitoring storage stability of three mAbs in a DP as a function of time (months). HIC-HPLC is used to quantitate the amount, and thus the concentration, of each of the three mAbs at six points in time over one year. An example set of data points from one time point in this study includes a measurement of the concentration of mAb A at 16.6 mg/mL, the concentration of mAb B at 17.5 mg/mL, and mAb C at 17.1 mg/mL. In this case, the storage stability shows that over the time period monitored, there is no appreciable change in concentration of each of the mAbs (≤4%).

The HIC-HPLC method has acceptable repeatability (≤0.2%), intermediate precision (≤1.7%), accuracy (93%-106% recovery) and linearity ($R^2 \geq 0.999$) over the range of 100 to 300 µg (each individual mAb) and can be used to determine the concentration of each of three mAbs in the cFDS and DP.

The HIC-HPLC method may be used as a release method for quantitating each of three mAbs in the co-formulated DS and DP. This method can also be used to support formulation development.

Example 4

Cation exchange ultra high-pressure liquid chromatography (CEX-UPLC) separation of a co-formulation comprising 3 anti-Ebola mAbs of similar molecular weights, protein structures, and charge properties is developed and evaluated.

The CEX-UPLC method uses a YMC-BioPro SP-F column with mobile phases including 200 mM MES buffer and 10 to 120 mM NaCl gradient, with a pH of 6.5. A six-point standard calibration curve is prepared for each of three mAb molecules (mAb A, mAb B, mAb C). The linearity of each calibration curve is determined to have an $R^2 \geq 0.99$. The three mAb molecules are separated from a co-formulation (i.e., a mixture) using CEX-UPLC, and a chromatograph of the UPLC is generated. The chromatograph shows separation of each mAb, with some overlap between mAb A and mAb C.

The repeatability of the method is evaluated by analyzing triplicate samples of the co-formulation run in three different amounts (150 µg, 225 µg, and 300 µg). The accuracy (% recovery) is determined by comparing the measured concentrations for each sample to the theoretical value. A linear range of quantitation of each mAb is determined to be 50 to 100 µg for each antibody, except for mAb A, with $R^2 \geq 0.973$ and accuracy of 75%-91%.

Figure 15:
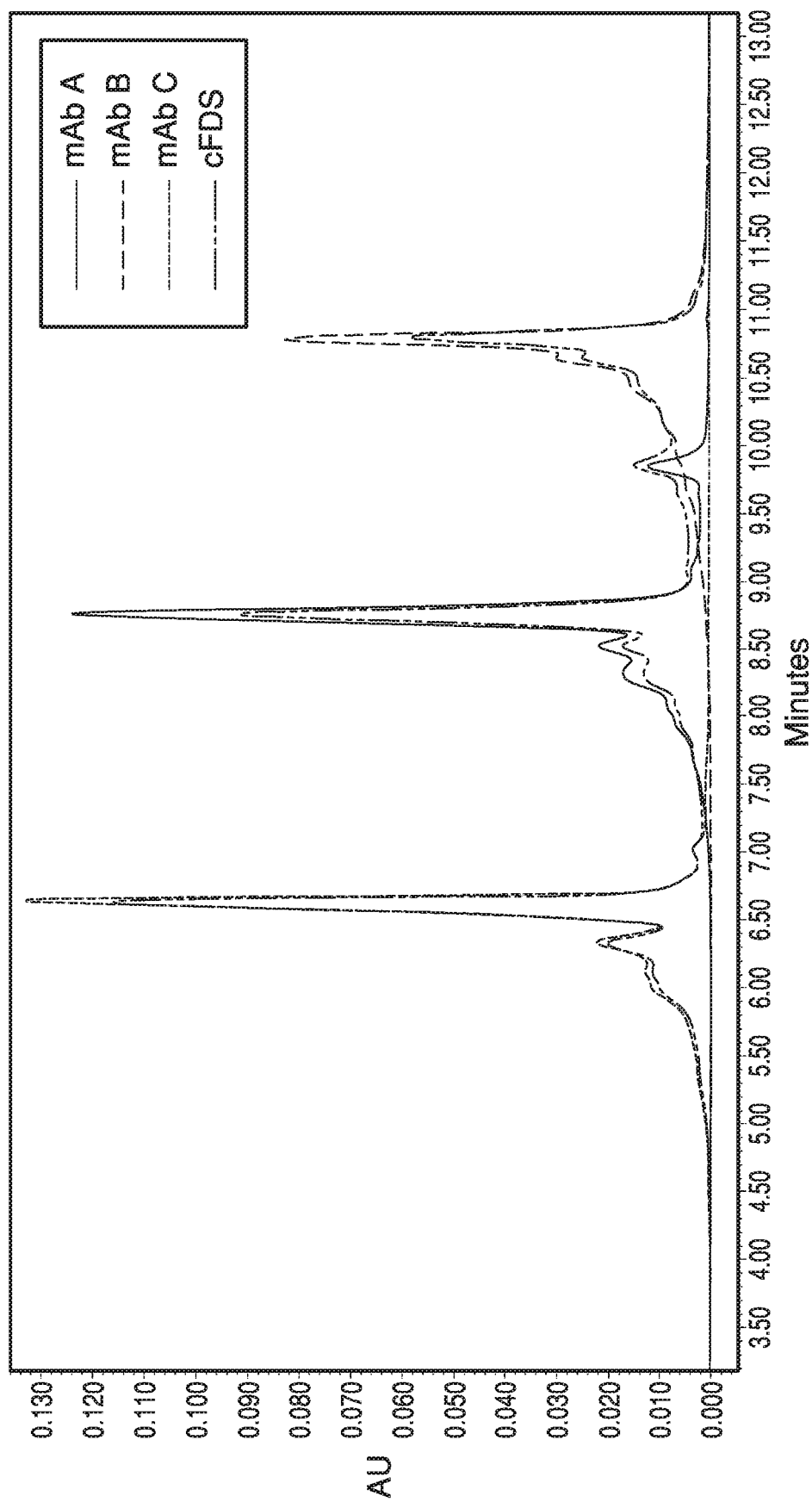
FIG. 15 shows an exemplary chromatograph of a cation exchange ultra high pressure liquid chromatography (CEX-UPLC) run of a co-formulation comprising anti-Ebola mAbs.

FIG. 15 shows a chromatograph of a CEX-UPLC run of separation of 3 mAbs from a co-formulation. The three antibodies are separated, with a small overlap between mAb A and mAb C.

Repeatability and Accuracy of CEX-UPLC

The repeatability is evaluated by analyzing samples of the cFDS in triplicate at five different percentages (25%-100%) of the target amount (600 µg/injection of cFDS). The RSD of repeatability is determined to be between 3.7% and 21.4%

TABLE 7

Repeatability and accuracy data

| Inject amount | Measured Concentration [mg/mL] | | | | | |
|---|---|---|---|---|---|---|
| | mAb A | | mAb B | | mAb C | |
| cFDS [µg] | RSD (n = 3) | % Recovery | RSD (n = 3) | % Recovery | RSD (n = 3) | % Recovery |
| 150 (50 per mAb) | 9.5% | 80% | 9.7% | 83% | 8.9% | 86% |
| 225 (75 per mAb) | 3.7% | 91% | 5.0% | 89% | 3.7% | 91% |
| 300 (100 per mAb) | 21.4%* | 75% | 5.2% | 91% | 4.9% | 90% |

*These data points were out of analytical range of the method

Linearity of CEX-UPLC

Figure 16:
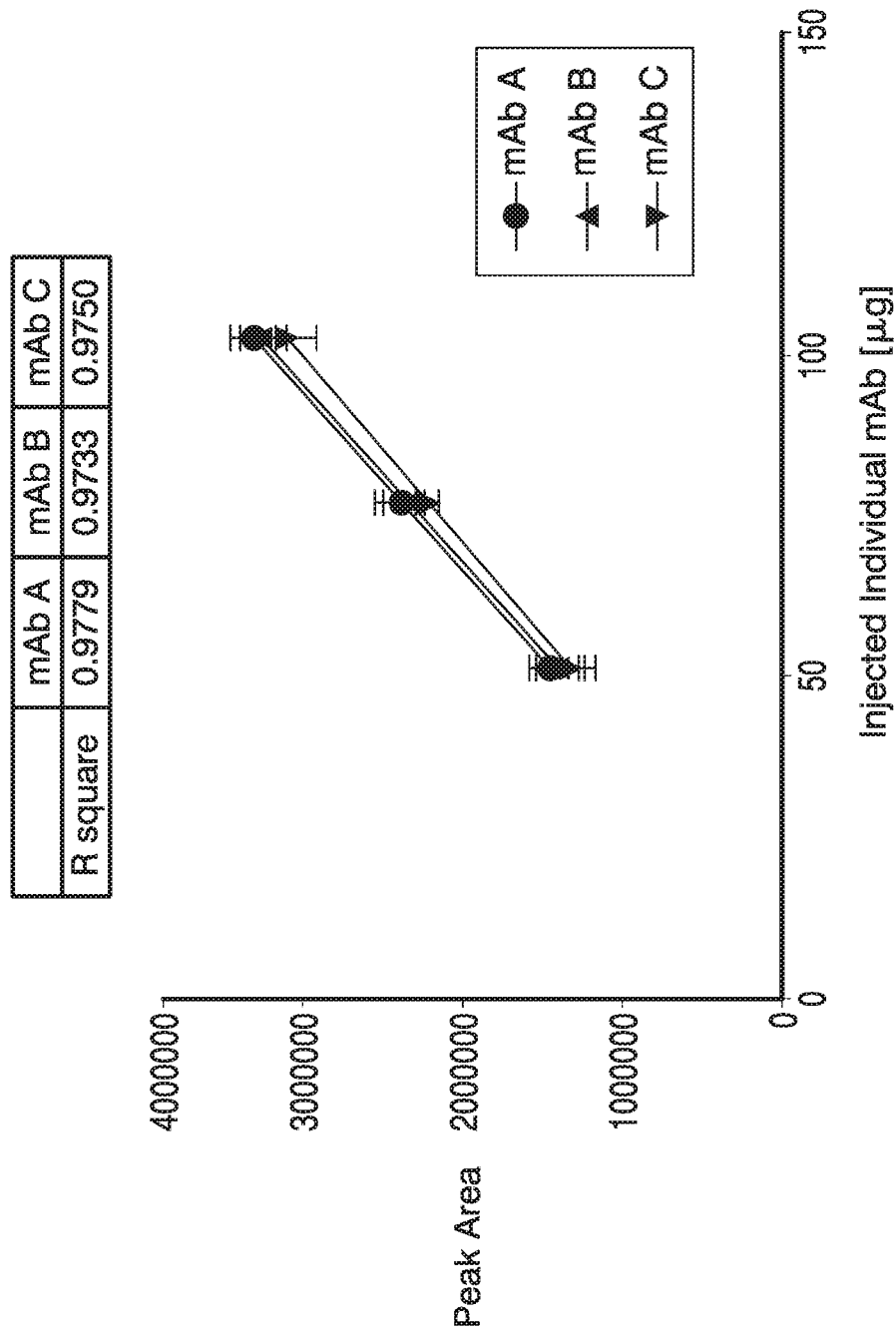
FIG. 16 is a plot of linearity of CEX-UPLC, plotting peak area against amount of individual anti-Ebola mAb.

Data from the repeatability study is used to evaluate the range and linearity of the CEX-UPLC method. A plot (FIG. 16) of the peak area of individual mAb versus the injected amount generally results in a linear curve for each mAb. However, because the RSD for mAb is over 10%, the data point for mAb A at 100 µg is not sufficiently statistically significant to conclude that a linear curve extending to 100 µg exists for mAb A.

Range of CEX-UPLC

Some repeatability (RSD≤10%), accuracy (>80%) and linearity ($R^2 \geq 0.97$) is shown for the cFDS sample from 150 to 300 µg in total antibody quantity. However, a range for CEX-UPLC is not as clearly shown as for HIC-HPLC.

TABLE 8

HIC-HPLC data summary

| Repeatability (n = 3) | mAb A | ≤0.1% |
|---|---|---|
| | mAb B | ≤0.2% |
| | mAb C | ≤0.2% |
| Accuracy (% Recovery) | mAb A | 80-91% |
| | mAb B | 83-91% |
| | mAb C | 86-91% |
| Linearity | $R^2 \geq 0.97$ | |
| | (a plot of the peak area of each mAb versus the injected individual mAb amount in cFDS at 50 to 100 µg range) | |
| Standard Curve | $R^2 \geq 0.99$ | |
| | (25-250 µg of individual mAb standard) | |
| Range | mAb A | 50 to 75 µg |
| | mAb B | 50 to 100 µg |
| | mAb C | 50 to 100 µg |

The CEX-UPLC method separates three mAbs based on their charge properties, with some overlap. The overlap means that manual integration of the method is needed. The precision, accuracy, and range of CEX-UPLC is not as optimal as HIC-HPLC.

Example 5

Figure 17:
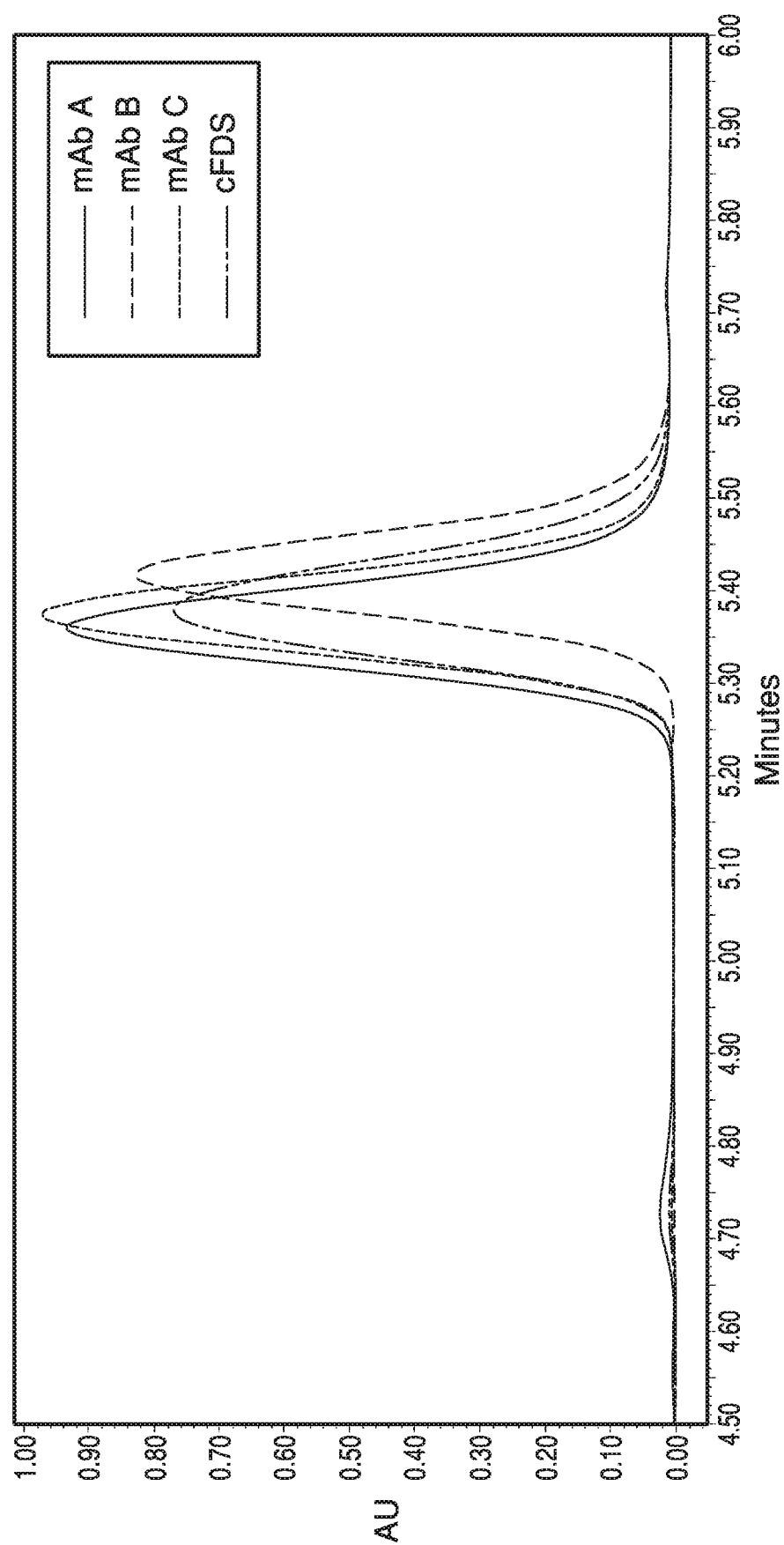
FIG. 17 shows an exemplary chromatograph of a size-exclusion ultra high pressure liquid chromatography (SE-UPLC) run of a co-formulation comprising anti-Ebola mAbs.

SE-UPLC of the co-formulation comprising the three anti-Ebola mAbs of similar molecular weight is evaluated. SE-UPLC separates mAbs by size. A Waters Acquity H UPLC system is used. Two Waters BEH200 SEC columns are linked in series. The mobile phase includes 10 mM Phosphate buffer at pH 6.0, and 1 M Perchlorate. FIG. 17 depicts a chromatogram of the SE-UPLC. As shown, there is significant overlap between elution times of the three mAbs. Thus, SE-UPLC is a sub-optimal method for separating the three anti-MERS mABs of similar molecular weight.

Figure 18:
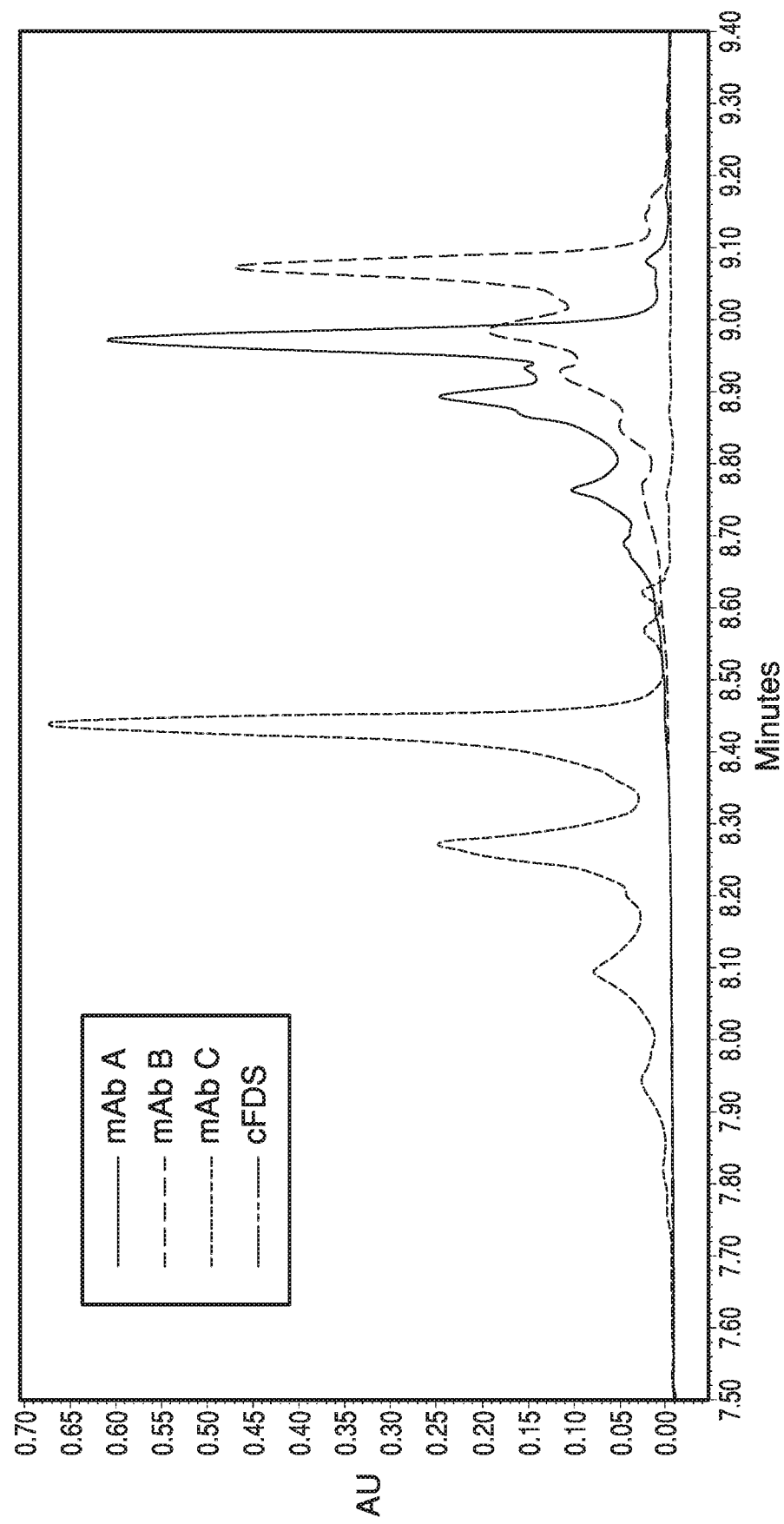
FIG. 18 shows an exemplary imaged capillary isoelectric focusing (iCIEF) profile of a co-formulation comprising anti-Ebola mAbs.

Example 6 iCIEF of the co-formulation comprising the three anti-Ebola mAbs of similar molecular weights, protein structures, and charge properties is evaluated. iCIEF separates proteins by their isoelectric point (pI). A ProteinSimple iCE3 charge variant analyzer is used. 4% pH 3-10 Pharmalyte® is used as an ampholyte, and 2M urea is used as a buffer. FIG. 18 depicts an iCIEF profile generated using these specifications. As shown, there is significant overlap between elution times of mAb A and mAb C. Thus, iCIEF is a sub-optimal method for separating the three anti-MERS mABs.

Example 7

Figure 19:
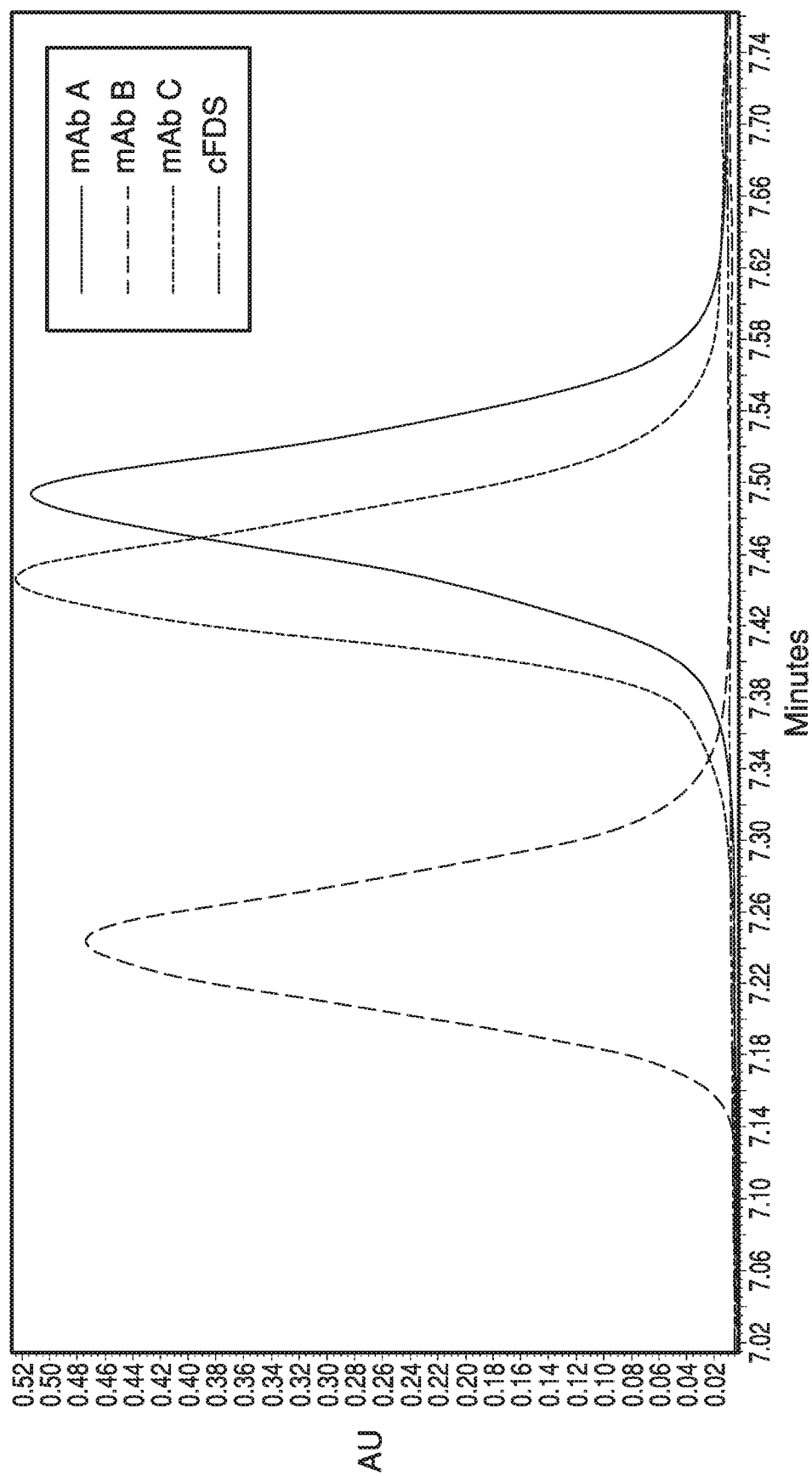
FIG. 19 shows an exemplary chromatograph of a reverse phase ultra high pressure liquid chromatography (RP-UPLC) run of a co-formulation comprising anti-Ebola mAbs.

RP-UPLC of the co-formulation comprising the three anti-Ebola mAbs of similar molecular weights, protein structures, and charge properties is evaluated. RP-UPLC separates mAbs by hydrophobicity. A Waters Acquity UPLC system is used. A ZORBAX 300SB-C8 column is used, and the column is run at 80° C. The mobile phase includes 60-90% acetonitrile in 0.1% TFA. FIG. 19 depicts a chromatogram of the RP-UPLC. As shown, there is significant overlap between elution times of mAb A and mAb B. Thus, RP-UPLC is a sub-optimal method for separating the three anti-MERS mAbs of similar molecular weight.

EMBODIMENTS

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A method of quantitating antibodies in a mixture comprising a plurality of antibodies, the method comprising:
    generating a standard curve for each antibody of the plurality of antibodies;
    separating each antibody of the plurality of antibodies by using hydrophobic interaction chromatography high performance liquid chromatography (HIC-HPLC); and
    after separating each antibody, quantitating an amount of each antibody using the standard curve;
    wherein two or more of the antibodies in the mixture are of the same isotype.

2. The method of claim 1, wherein the plurality of antibodies includes a first antibody and a second antibody, and wherein:
    a first antibody in the mixture and a second antibody in the mixture have protein sequences that are at least 90% homologous; and/or
    the first antibody and the second antibody have protein structures that are at least 90% homologous, as determined by their protein sequences.

3. The method of claim 1, wherein an isoelectric point of each antibody of the plurality of antibodies is within about 0.6 of an isoelectric point of all other antibodies in the mixture.

4. The method of claim 1, wherein one or more antibodies of the plurality of antibodies are monoclonal antibodies.

5. The method of claim 2, wherein a first antibody in the mixture elutes at a first run time during a HIC-HPLC run, a second antibody in the mixture elutes at a second run time during the HIC-HPLC run, and the first and second run times do not overlap.

6. The method of claim 1, wherein two or more of the antibodies in the mixture are variants of each other.

7. The method of claim 1, wherein two or more of the antibodies in the mixture bind to the same antigen.

8. A method of quantitating antibodies in a mixture comprising a plurality of antibodies, the method comprising:
    separating each of the plurality of antibodies in the mixture using hydrophobic interaction chromatography high performance liquid chromatography (HIC-HPLC); and
    quantitating an amount of each antibody in the mixture, wherein the mixture is a co-formulated composition.

9. The method of claim 8, wherein a molecular weight of each antibody in the mixture is within 15 kDa of a molecular weight of all other antibodies in the mixture.

10. The method of claim 8, further comprising determining a surface hydrophobicity of each antibody in the mixture.

11. The method of claim 10, wherein the surface hydrophobicity of each antibody in the mixture is different from the surface hydrophobicity of another antibody in the mixture by about 0.25 to about 1.0 units on the Kyte & Doolittle hydropathy scale.

12. The method of claim 10, wherein the surface hydrophobicity of each antibody in the mixture is determined by calculating the surface hydrophobicity based on the primary protein structure of the antibody.

13. The method of claim 8, wherein each antibody in the mixture, when run on HIC-HPLC individually, elutes at a distinct run time from another antibody in the mixture.

14. The method of claim 8, wherein the co-formulated composition is configured to treat macular degeneration in a human patient.

15. The method of claim 8, wherein the co-formulated composition is configured to treat an infectious disease in a human patient.

16. A method of quantitating antibodies in a mixture comprising a plurality of antibodies, the method comprising:
    generating a standard curve for each antibody of the plurality of antibodies;
    separating each antibody of the plurality of antibodies by using hydrophobic interaction chromatography high performance liquid chromatography (HIC-HPLC), wherein each antibody elutes at a distinct run time from other antibodies of the of antibodies, when individually run on HIC-HPLC;
    generating a chromatograph from the HIC-HPLC, wherein for elution of each antibody in the mixture, the chromatograph shows a peak that does not overlap with other peaks in the chromatograph; and
    quantitating an amount of each antibody of the plurality of antibodies.

17. The method of claim 16, wherein one or more of the monoclonal antibodies in the mixture are human monoclonal antibodies.

18. The method of claim 16, wherein the plurality of antibodies comprises three antibodies.

19. The method of claim 16, wherein the plurality of antibodies includes a first antibody and a second antibody, the first antibody elutes at a first run time, the second antibody elutes at a second run time, and the first and second run times do not overlap.

20. The method of claim 16, wherein each antibody in the mixture elutes at a distinct run time from each other antibody in the mixture, based on differences in surface hydrophobicity of the antibodies.

* * * * *

UNITED STATES PATENT AND TRADEMARK OFFICE
CERTIFICATE OF CORRECTION

PATENT NO. : 11,850,535 B2
APPLICATION NO. : 18/067803
DATED : December 26, 2023
INVENTOR(S) : Dingjiang Liu, Lin Luo and Long Xu It is certified that error appears in the above-identified patent and that said Letters Patent is hereby corrected as shown below:

On the Title Page

In Column 2, Line 13, Item (57) in the Abstract, delete "nm" and insert --run--.

In the Claims

Column 20, Line 39, in Claim 16, after "of the" delete "of".

Signed and Sealed this
Twenty-seventh Day of August, 2024

Katherine Kelly Vidal
*Director of the United States Patent and Trademark Office*